(12) United States Patent
Sassano et al.

(10) Patent No.: US 8,883,446 B2
(45) Date of Patent: Nov. 11, 2014

(54) HUMAN LONG PENTRAXIN 3 EXPRESSION SYSTEM AND USES THEREOF

(75) Inventors: Marica Sassano, Caserta (IT); Adelaide Esposito, Grumo Nevano (IT); Vincenzo Rivieccio, Torre del Greco (IT); Giovanni Cassani, Pavia (IT)

(73) Assignee: Sigma-Tau Industrie Farmaceutiche Riunite, S.p.A., Rome (IT)

( * ) Notice: Subject to any disclaimer, the term of this patent is extended or adjusted under 35 U.S.C. 154(b) by 249 days.

(21) Appl. No.: 13/387,784

(22) PCT Filed: Jul. 20, 2010

(86) PCT No.: PCT/EP2010/060469
§ 371 (c)(1), (2), (4) Date: Jun. 13, 2012

(87) PCT Pub. No.: WO2011/012496
PCT Pub. Date: Feb. 3, 2011

(65) Prior Publication Data
US 2012/0301873 A1    Nov. 29, 2012

(30) Foreign Application Priority Data
Jul. 29, 2009    (EP) .................................... 09166759

(51) Int. Cl.
| | | |
|---|---|---|
| *C12N 5/22* | (2006.01) | |
| *C12N 15/63* | (2006.01) | |
| *C12N 15/85* | (2006.01) | |
| *C12P 21/02* | (2006.01) | |
| *C07K 14/71* | (2006.01) | |
| *C12N 5/16* | (2006.01) | |
| *C12N 15/67* | (2006.01) | |
| *C12N 15/79* | (2006.01) | |

(52) U.S. Cl.
CPC ................ *C12N 15/85* (2013.01); *C07K 14/71* (2013.01); *C12N 5/16* (2013.01); *C12N 15/67* (2013.01); *C12N 15/79* (2013.01); *C12N 2800/106* (2013.01); *C12N 2830/50* (2013.01)

USPC ...... 435/69.1; 435/70.3; 435/455; 435/320.1; 435/369

(58) Field of Classification Search
None
See application file for complete search history.

(56) References Cited

U.S. PATENT DOCUMENTS

2003/0203447 A1 * 10/2003 Horwitz ....................... 435/69.1

FOREIGN PATENT DOCUMENTS

| EP | 1832295 A1 | 9/2007 |
|---|---|---|
| WO | WO 2009095403 A1 * | 8/2009 |

OTHER PUBLICATIONS

FreeStyle™ 293 Expression System Manual for Protein production in mammalian cells, Invitrogen, Life Technologies, 2002, printed as pp. 1/4-4/4.*
Bottazzi, B., et al., "Multimer Formation and Ligand Recognition by the Long Pentraxin PTX3", The Journal of Biological Chemistry, vol. 272, No. 52, Dec. 1997, pp. 32817-32823.
Durocher, Y., et al., "High-Level and high-throughout recombinant protein production by transient transfection of suspension-growing human 293-EBNA1 cells", Nuclear Acids Research, vol. 30, No. 2, Jan. 2002, 9 pages.
Rivieccio, V., et al., "High-level expression and efficient purification of recombinant human long pentraxin PTX3 in Chinese hamster ovary cells", Protein Expression and Purification Academic Press, vol. 51, No. 1, Nov. 2006, pp. 49-58.

* cited by examiner

*Primary Examiner* — Jennifer Dunston
(74) *Attorney, Agent, or Firm* — Lucas & Mercanti, LLP

(57) ABSTRACT

The present invention relates to an eukaryotic expression vector comprising a nucleotide sequence encoding for the human long pentraxin PTX3 protein under the control of an effective promoter and a nucleotide sequence encoding for a selectable marker, recombinant human cell able to provide expression of proteins encoded by the vector and method for the production of the human long pentraxin PTX3 protein.

16 Claims, 5 Drawing Sheets

Figure 1:
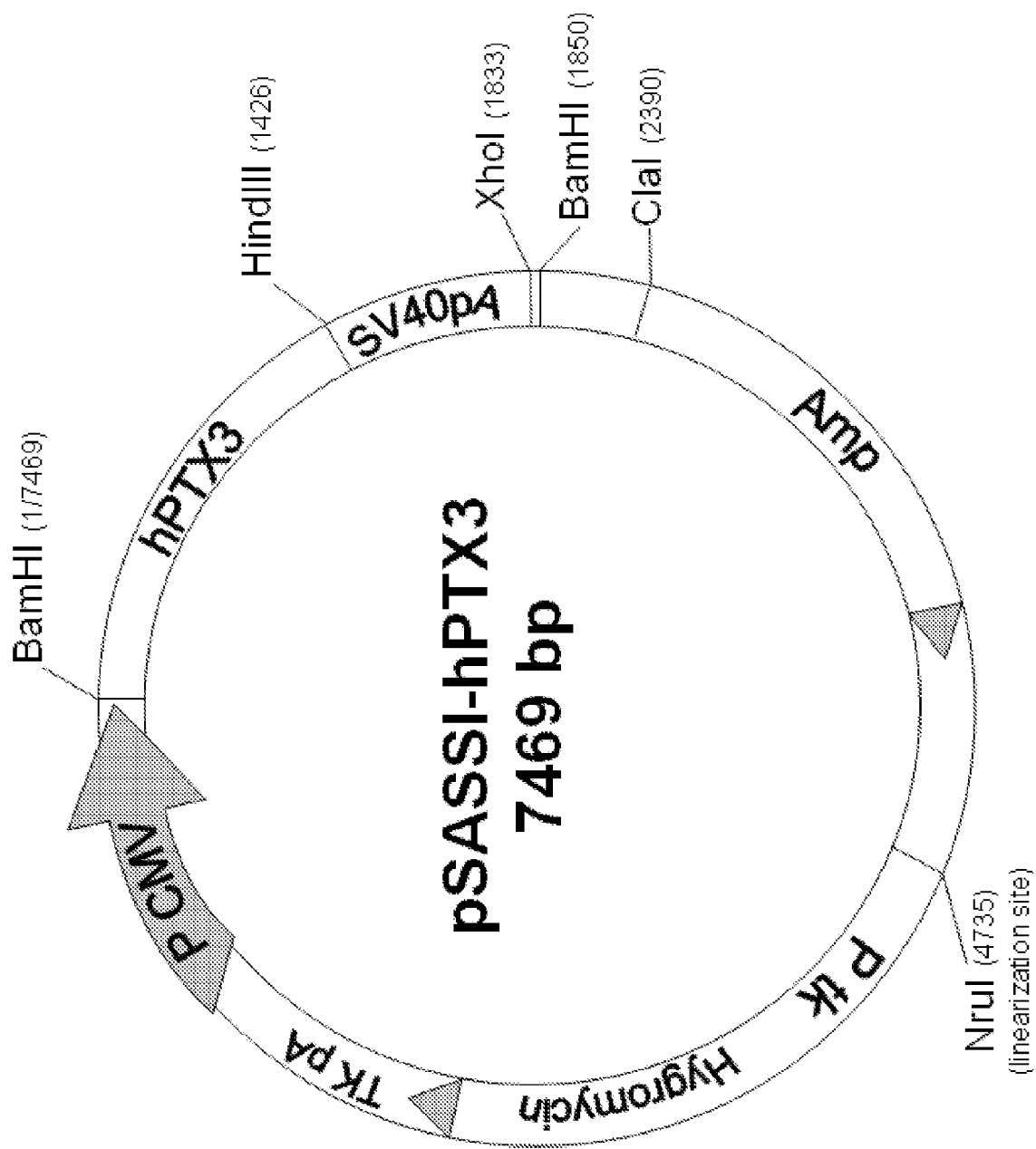

| Features | Nucleotide position |
| --- | --- |
| hPTX3 ORF | 100-1245 |
| Bgl II | 1475 |
| SV40 polyA signal | 1489-1622 |
| SV40 promoter and origin of replication | 1765-2090 |
| Neo ORF | 2126-2907 |
| SV40 polyA signal | 3095-3225 |
| pUC origin of replication | 3233-3899 |
| Ampicillin resistance (*bla*) ORF | 4051-4908 |
| Human ubiquitin C (*UbC*) promoter | 5578-6787 |

HUMAN LONG PENTRAXIN 3 EXPRESSION SYSTEM AND USES THEREOF

This application is a U.S. national stage of PCT/EP2010/060469 filed on Jul. 20, 2010 which claims priority to and the benefit of European Application No. 09166759.2 filed on Jul. 29, 2009, the contents of which are incorporated herein by reference.

FIELD OF THE INVENTION

The present invention relates to human derived cellular system able to express high levels of the human pentraxin 3 (hPTX3) protein, methods and material used.

BACKGROUND TO THE INVENTION

Human long pentraxin 3, PTX3 or hPTX3 (GENBANK ® Accession Number BD 131701) is a multimeric glycoprotein composed of eight subunits linked by disulphide bridges.

The authors of the present invention have already designed an expression system for the production of PTX3 in HEK293F human cell line. This system is based on a plasmid containing the neomycin resistance gene wherein the PTX3 gene is under the control of a human Ubiquitin C promoter sequence. Such system avoids the potential formation of a chimeric PTX3 derived from endogenous production of PTX3 by a cell line of non-human origin. The best producer isolated clone, named 2F12, was selected among those obtained. A production of about 20 mg/L of PTX3 was obtained, which was not sufficient for commercial production needs.

With the aim to increase PTX3 expression levels, the authors of the present invention have constructed a plasmid in which the PTX3 gene was under CMV promoter control. The plasmid was used to re-transfect the PTX3 expressing clone 2F12. The productivity level detected in the new isolated transfectomas was higher that expected, around 80 mg/L.

DESCRIPTION OF THE INVENTION

A clone of human origin expressing high levels of human PTX3 was obtained using an experimental strategy, including the following steps:
a) construction of plasmid expression cassettes carrying the human PTX3 under the control of CMV promoter;
b) insertion of the hygromycin resistance cassette in said plasmid, in order to select stable transfectomas originating from a re-transfection of PTX3 expressing clone G418 resistant;
c) verifying the identity and the levels of expressed recombinant proteins;
d) biochemical characterization of the recombinant hPTX3.

The content of PCT/EP2009/050937 is hereby incorporated by reference.

It is an object of the invention an eukaryotic expression vector comprising a nucleotide sequence encoding for the human long pentraxin PTX3protein under the control of an effective promoter and a nucleotide sequence encoding for a selectable marker, having essentially the sequence of SEQ ID NO: 1.

The vector is preferentially use to transform host cell, preferably wherein the host cell is a recombinant human cell already able to express the human long pentraxin PTX3 protein, more preferably wherein the recombinant human cell is the recombinant 293F/PTX3/2F12 clone deposited at ECACC with no. 08011001. In a particular aspect the vector is linearized.

It is another object of the invention a recombinant cell able to express the human long pentraxin PTX3 protein encoded by the vector as above disclosed, preferably it is recombinant HEK293F cell line, more preferably it is the recombinant MS24PTX clone deposited at Health Protection Agency, Culture Collections Centre For Emergency Preparedness and Response Salisbury UK, with no. 09072902.

It is another aspect of the invention the use of the recombinant cell as above disclosed for the production of human long pentraxin PTX3 protein.

It is another object of the invention a process for the production of the recombinant human long pentraxin PTX3 protein comprising:
a) transfecting a recombinant human cell already expressing recombinant human long pentraxin PTX3 protein, with a selectable plasmid in which the human long pentraxin gene is under the control of the CMV promoter;
b) selecting and growing transfected recombinant human cell;
c) purifying the human long pentraxin PTX3 protein from the culture medium of the transfected recombinant human cell.

Preferably the recombinant human cell expressing a recombinant human long pentraxin PTX3 protein is a recombinant HEK293F cell line, more preferably it is the recombinant 293F/PTX3/2F12 clone deposited at ECACC under number 08011001.

In a preferred embodiment the purification step includes at least one of the following step: anionic-exchange chromatography, hydroxyapatite chromatography or size exclusion chromatography.

It is another object of the invention a process for the production of the recombinant human long pentraxin PTX3protein comprising:
a) co-transfecting contemporarily or sequentially human cells with a first vector having essentially the sequence of SEQ ID NO: 1and a second vector having essentially the sequence of SEQ ID NO: 2;
b) selecting and growing the double transfected cells;
b) purifying the human long pentraxin PTX3protein from the culture medium of double transfected cells.

It is another object of the invention a process for the production the recombinant human long pentraxin PTX3 protein comprising the step of growing the recombinant MS24PTX clone and purifying the human long pentraxin PTX3 protein from the culture medium.

Figure 3:
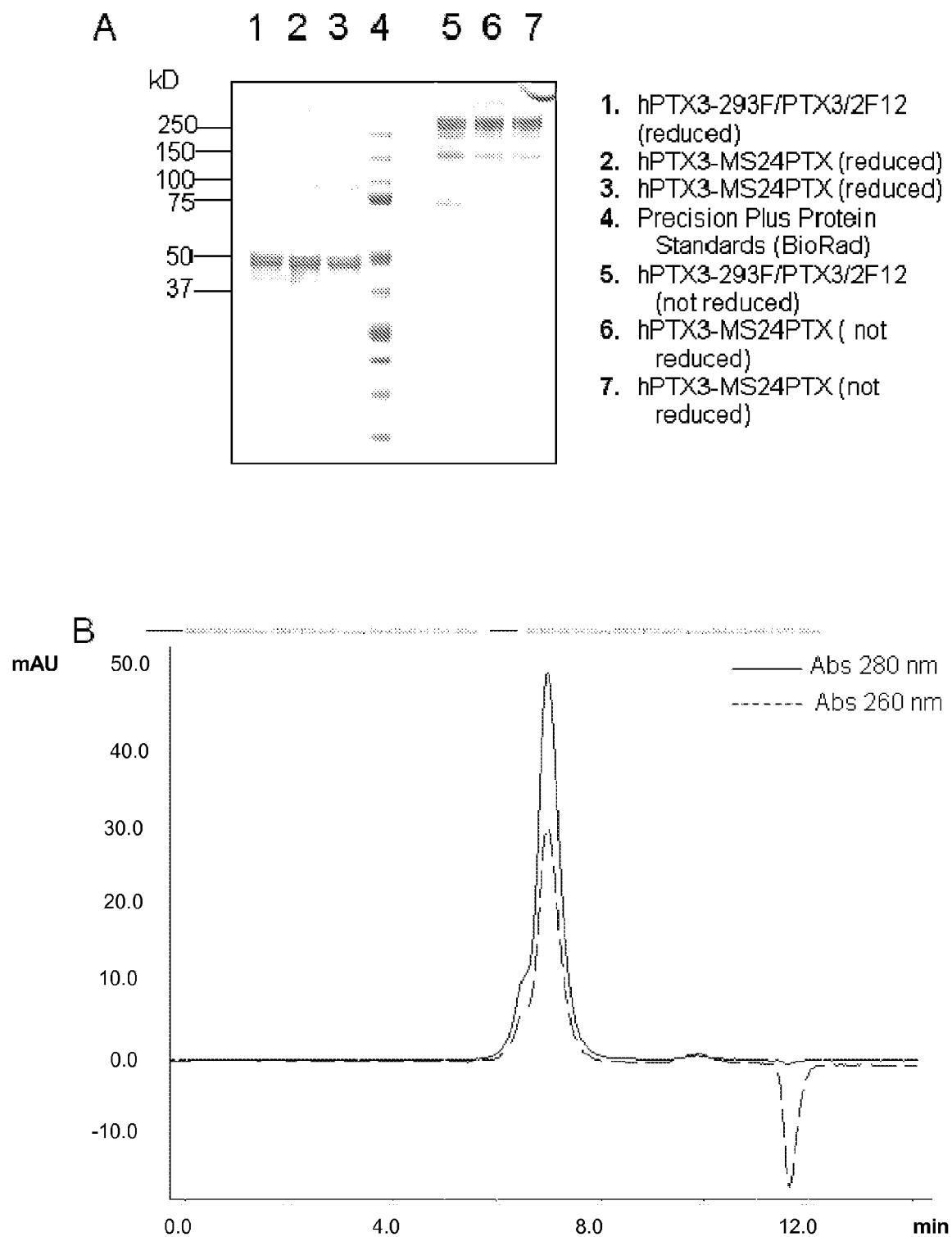
Figure 4:
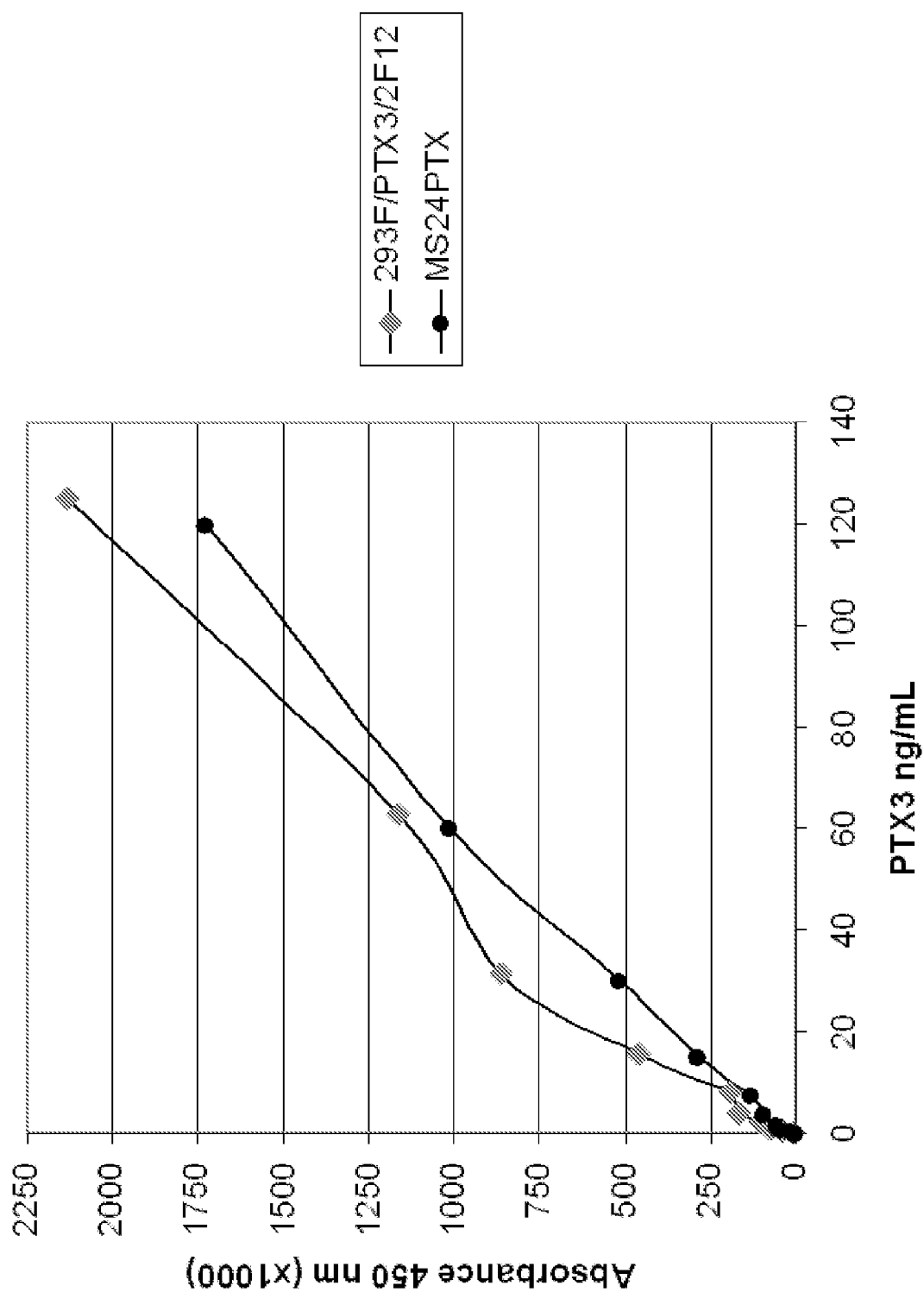
Figure 5:
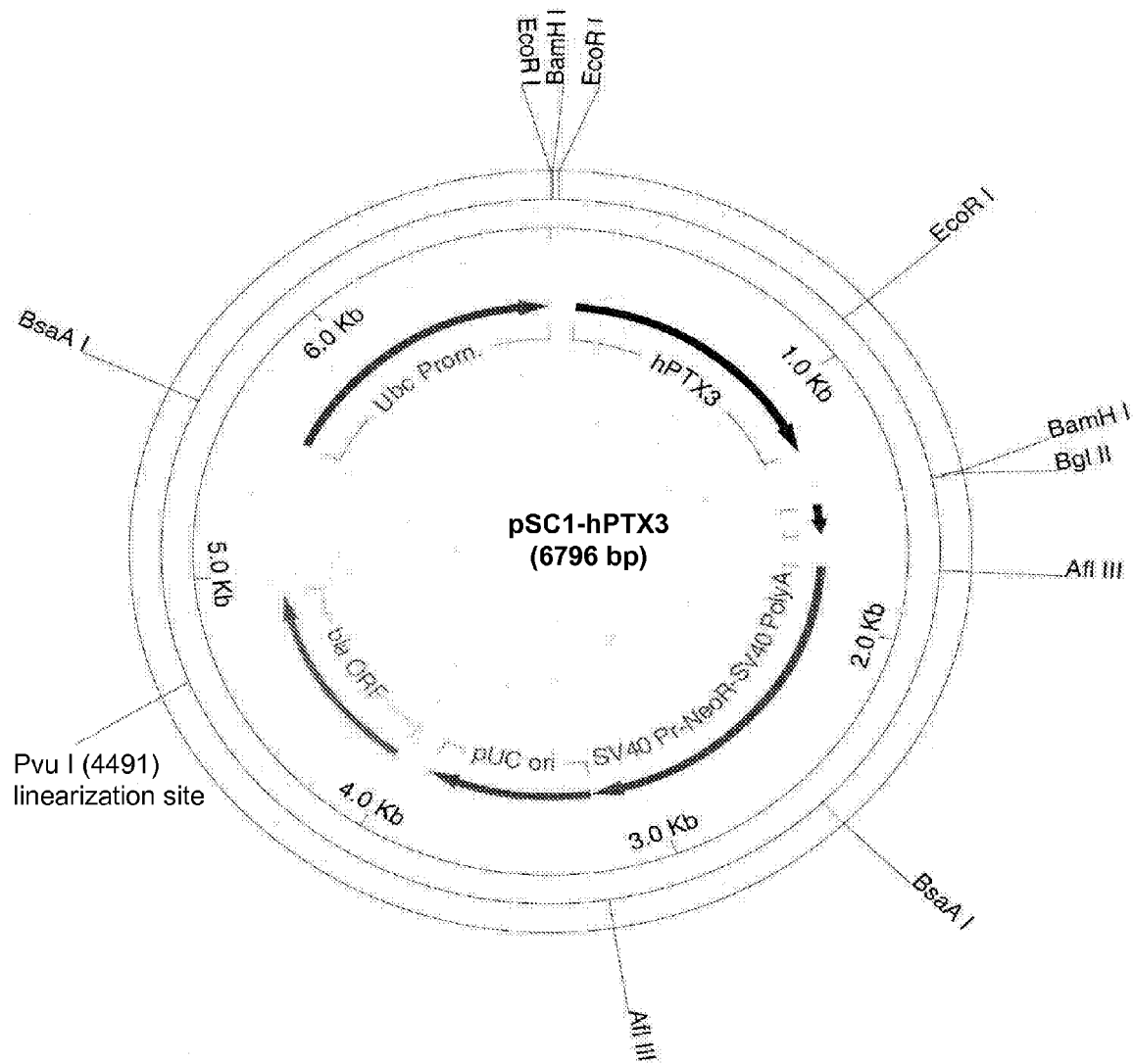

The invention will be now illustrated by means of non limiting examples, referring in particular to the following figures:
FIG. 1: pSASSI-hPTX3 map and main features
FIG. 2: Growth, viability and productivity in Spinner Flask of (A) MS24PTX clone and (B) 293F/PTX3/2F12 clone.
FIG. 3: characterization by SDS-PAGE gradient 4-15% (A) and Size Exclusion Chromatography (B) of recombinant human PTX3 purified from MS24PTX clone.
FIG. 4: FGF2 binding capability of hPTX3 clone 293F/PTX3/2F12 and hPTX3 clone MS24PTX.
FIG. 5: pSC1-hPTX3 map and main features.

EXAMPLES

Example 1

Clone 293F/PTX3/2F12

Construction of the Plasmid pSC1-PTX3
1. Construction of pSG/Ub 1.1 Preparation of the Human Ubiquitin C Promoter Sequence The human ubiquitin C promoter is taken from pUB/Bsd plasmid (Invtrogen, Cat. n. V512-20), by amplification with PCR. As part of the cloning strategy, recognition sequences for restriction endonucleases are introduced at both ends. A BsaAI site is built in the upstream amplification primer and an EcoRI site in the downstream primer. The amplified region corresponds to nucleotides 1941 to 3161 in the sequence of pUB/Bsd.

The oligonucleotides are designed as follows:

```
5'p UbC: length: 26mer
                                   (SEQ ID NO: 3)
ATATCACGTG ATC TGG CCT CCG CGC C 3'p UbC: length: 23mer
                                   (SEQ ID NO: 4)
GGAATTC GGT CCG GTC TAA CAA A
```

The protocol for amplification is the following: 1 ng/µl of plasmid DNA, 2 mM MgCl2, 0.2 mM dNTPs, 400 nM of each primer, 1× supplied buffer and 0.04 u/ml of Taq DNA polymerase (Sigma Genosys); temperature profile: 3 min 94° C., 30 times (30 sec. 94° C., 30 sec. 46° C., 2 min 72° C.), 5 min 72° C., cooling at 4° C. until further use.

The amplification product (1238 bp) is purified by silica membrane spin column (NucleoSpin, Machery-Nagel GmbH & Co.), ligated in pGEM-T-Easy vector (Promega Cat. n. A1360) and transformed into *E. coli* host strain HB2151 (Pharmacia Biotech). Transformants are selected by growth on LB medium supplemented with 50 mg/l ampicillin Plasmids DNA, isolated from ampicillin resistant colonies, are checked by restriction analysis with StuI plus SacI enzymes (expected ~3650 and 600 bp fragments)

Plasmids showing the correct restriction pattern are further checked by sequence analysis of the entire insert and subsequently digested with EcoRI (Sigma-Genosys) and BsaAI (New England Biolabs) restriction enzymes.

Human Ubiquitin C promoter is purified via agarose gel separation and elution on silica membrane spin column.

1.2 Preparation of the Vector Fragment pSG5

Plasmid pSG5 (4076 bp, Stratagene) was cut with the restriction enzymes EcoRI (Sigma-Genosys) and BsaAI (New England Biolabs); the resulting fragments are 1432 and 2644 bp long. The 2644 bp fragment, containing the backbone of pSG5, was prepared and purified via agarose gel electrophoresis plus silica membrane spin column.

1.3 Preparation of pSG/Ub

DNA fragments prepared in steps 1.1 and 1.2 were ligated using T4 DNA ligase (Promega) and transformed in HB2151 *E. coli* cells. Transformants were selected by growth on LB medium supplemented with 50 mg/l ampicillin.

Plasmid DNA, isolated from ampicillin resistant colonies, was checked by restriction analysis with EcoRI plus SacII enzymes (expected: 2670 and 1192 bp fragments). A plasmid DNA, with the expected restriction pattern, was designed as pSG/Ub.

2. Construction of pSC1

2.1 Preparation of the Neomycin Resistance Cassette (NeoR)

The Neomycin Resistance Cassette (NeoR) was taken from pcDNA3 plasmid (5446 bp, Invitrogen), amplifying it by PCR. As part of the cloning strategy, recognition sequences for restriction endonuclease AflIII were introduced at both ends. The amplified region corresponds to nucleotides 1788 to 3252 in the sequence of pcDNA3 and includes the SV40 promoter and origin of replication, the neomycin resistance ORF, and the SV40 poliA signal.

The oligonucleotides are designed as follows:

```
5'NeoR
                                   (SEQ ID NO: 5)
ATATACATG TCC CCA GGC AGG CAG AA

3'NeoR
                                   (SEQ ID NO: 6)
ATATACAT GTAT ACA GAC ATG ATA AG
```

Protocol for amplification was the following: 1 ng/µl of plasmid DNA, 2 mM MgCl2, 0.2 mM dNTPs, 400 nM of each primer, 1× supplied buffer and 0.04 u/µl of Taq DNA polymerase (Sigma Genosys); temperature profile: 3 min 94° C., 30 times (30 sec. 94° C., 30 sec. 46° C., 2 min 72° C.), 5 min 72° C., cooling at 4° C. until further use.

The amplification product (1484 bp) was purified by silica membrane spin column, ligated in pGEM-T-Easy vector (Promega Cat. n. A1360) and transformed into *E. coli* host strain HB2151. Transformants are selected by growth on LB medium, supplemented with 50 mg/l ampicillin Plasmids DNA, isolated from ampicillin resistant colonies, are checked by restriction analysis with SmaI plus SacI enzymes (expected ~1200 and 3300 bp fragments).

Plasmids showing the correct restriction pattern were further checked by sequence analysis of the entire insert and subsequently digested with AflIII (New England Biolabs) restriction enzymes. NeoR cassette (1471 bp) was purified via agarose gel separation and elution on silica membrane spin column.

2.2 Preparation of the Vector Fragment pSG/Ub

Plasmid pSG/Ub, prepared in step 1.3, was linearized by AflIII digestion and purified on silica membrane spin column.

2.3 Preparation of pSC1 DNA fragments prepared as in steps 2.1 and 2.2 were ligated using T4 DNA ligase (Promega) and transformed in JM109 *E. coli* strain (New England Biolabs). Transformants were selected by growth on LB medium, supplemented with 50 mg/l ampicillin.

Antibiotic resistant colonies were preliminarliy analyzed by PCR amplification with 5'NeoR and 3'NeoR oligonucleotides, as previously described, and subsequently, purified plasmids were checked by restriction analysis. For this purpose, SmaI (position 602, inside NeoR sequence) and SacII (position 4142, inside UbC sequence) enzymes were used. A plasmid DNA, with the expected restriction pattern (3540 and 1793 bp fragments), was designed as pSC1.

3. Construction of pSC1-PTX3

3.1 Preparation of the hPTX3 Coding Sequence

The hPTX3(GENBANK® Accession Number BD 131701) sequence was taken from pSG5PTX3(WO 99/32516"Pharmaceutical compositions containing the long pentraxin PTX3) by BamHI (Roche Applied Science) digestion. Human PTX3fragment (1463bp) was purified by agarose gel electrophoresis and silica membrane spin column.

3.2 Preparation of the Vector Fragment pSC1

The pSC1 vector was linearized by BamHI digestion and purified on silica membrane spin column.

3.3 Construction and Verification on pSC1-PTX3

DNA fragments prepared in steps 3.2 and 3.3 were ligated using T4 DNA ligase (Roche Applied Science) and transformed in JM109*E. coli* strain. Transformants were selected by growth on LB medium, supplemented with 50 mg/l ampicillin and preliminarily screened by PCR with two oligonucleotides complementary to PTX3 sequence.

The oligonucleotides sequences are:

```
5'PTX
                                    (SEQ ID NO: 7)
GTGAGAACTCGGATGATTATGAT

3'PTX
                                    (SEQ ID NO: 8)
TGAAACATACTGAGCTCCTCCAT
```

In a final volume of 10 μl, reagents for amplification were: 1 μl of boiled colony (1 colony in 50 ml of water), 2 mM MgCl2, 0.2 mM dNTPs, 320 nM of each primer, 0.06% Formamide, 1× supplied buffer and 0.08 u/μl of Taq DNA polymerase (Sigma Genosys); temperature profile: 3 min 96° C., 30 times (30 sec. 94° C., 30 sec. 58° C., 2 min 72° C.), 5 min 72° C., cooling at 4° C. until further use.

Plasmid purified from colonies positive to PCR screening, were digested with SalI restriction enzyme (Roche Applied Science) to check the orientation of hPTX3 insert. A plasmid with the expected restriction pattern (6619 and 177 bp) was sequenced in the regions coding for UbC promoter, NeoR cassette and hPTX3 and identified as pSC1-PTX3.

The new plasmid (pSC1-PTX3) was then constructed with PTX3 cDNA sequence located under ubiquitin promoter control and neomycin resistance gene under SV40 promoter control; all other features and plasmid map are represented in FIG. 1.

The complete sequence of pSC1-PTX3is as follows (SEQ NO: ID 2). The pSC1-hPTX3sequence is represented starting from the first EcoRI site (FIG. 5). The sequence deriving from pSG5containing PTX3cDNA is underlined. The starting codon (ATG) and termination codon are in bold.

pSC1-PTX3 (SEQ ID NO:2)

```
pSC1-PTX3
                                                                    (SEQ ID NO: 2)
AATTCGGATCCCCCGGGCTGCAGGAATTCCGGCTCAAACTCAGCTCACTTGAGAGTCTCCTCCCGCCAGCTGTGGAA

AGAACTTTGCGTCTCTCCAGCAATGCATCTCCTTGCGATTCTGTTTTGTGCTCTCTGGTCTGCAGTGTTGGCCGAGA

ACTCGGATGATTATGATCTCATGTATGTGAATTTGGACAACGAAATAGACAATGGACTCCATCCCACTGAGGACCCC

ACGCCGTGCGACTGCGGTCAGGAGCACTCGGAATGGGACAAGCTCTTCATCATGCTGGAGAACTCGCAGATGAGAGA

GCGCATGCTGCTGCAAGCCACGGACGACGTCCTGCGGGGCGAGCTGCAGAGGCTGCGGGAGGAGCTGGGCCGGCTCG

CGGAAAGCCTGGCGAGGCCGTGCGCGCCGGGGGCTCCCGCAGAGGCCAGGCTGACCAGTGCTCTGGACGAGCTGCTG

CAGGCGACCCGCGACGCGGGCCGCAGGCTGGCGCGTATGGAGGGCGCGGAGGCGCAGCGCCCAGAGGAGGCGGGGCG

CGCCCTGGCCGCGGTGCTAGAGGAGCTGCGGCAGACGCGAGCCGACCTGCACGCGGTGCAGGGCTGGGCTGCCCGGA

GCTGGCTGCCGGCAGGTTGTGAAACAGCTATTTTATTCCCAATGCGTTCCAAGAAGATTTTTGGAAGCGTGCATCCA

GTGAGACCAATGAGGCTTGAGTCTTTTAGTGCCTGCATTTGGGTCAAAGCCACAGATGTATTAAACAAAACCATCCT

GTTTTCCTATGGCACAAAGAGGAATCCATATGAAATCCAGCTGTATCTCAGCTACCAATCCATAGTGTTTGTGGTGG

GTGGAGAGGAGAACAAACTGGTTGCTGAAGCCATGGTTTCCCTGGGAAGGTGGACCCACCTGTGCGGCACCTGGAAT

TCAGAGGAAGGGCTCACATCCTTGTGGGTAAATGGTGAACTGGCGGCTACCACTGTTGAGATGGCCACAGGTCACAT

TGTTCCTGAGGGAGGAATCCTGCAGATTGGCCAAGAAAAGAATGGCTGCTGTGTGGGTGGTGGCTTTGATGAAACAT

TAGCCTTCTCTGGGAGACTCACAGGCTTCAATATCTGGGATAGTGTTCTTAGCAATGAAGAGATAAGAGAGACCGGA

GGAGCAGAGTCTTGTCACATCCGGGGGAATATTGTTGGGTGGGGAGTCACAGAGATCCAGCCACATGGAGGAGCTCA

GTATGTTTCATAAATGTTGTGAAACTCCACTTGAAGCCAAAGAAAGAAACTCACACTTAAAACACATGCCAGTTGGG

AAGGTCTGAAAACTCAGTGCATAATAGGAACACTTGAGACTAATGAAAGAGAGAGTTGAGACCAATCTTTATTTGTA

CTGGCCAAATACTGAATAAACAGTTGAAGGAAAGACATTGGAAAAAGCTTATCGATACCGTCGACCTCGAGGGGGGG

CCCGGGGATCCAGATCTTATTAAAGCAGAACTTGTTTATTGCAGCTTATAATGGTTACAAATAAAGCAATAGCATCA

CAAATTTCACAAATAAAGCATTTTTTTCACTGCATTCTAGTTGTGGTTTGTCCAAACTCATCAATGTATCTTATCAT

GTCTGGTCGACTCTAGACTCTTCCGCTTCCTCGCTCACTGACTCGCTGCGCTCGGTCGTTCGGCTGCGGCGAGCGGT

ATCAGCTCACTCAAAGGCGGTAATACGGTTATCCACAGAATCAGGGGATAACGCAGGAAAGAACATGTCCCCAGGCA

GGCAGAAGTATGCAAAGCATGCATCTCAATTAGTCAGCAACCAGGTGTGGAAAGTCCCCAGGCTCCCCAGCAGGCAG

AAGTATGCAAAGCATGCATCTCAATTAGTCAGCAACCATAGTCCCGCCCCTAACTCCGCCCATCCCGCCCCTAACTC

CGCCCAGTTCCGCCCATTCTCCGCCCCATGGCTGACTAATTTTTTTTATTTATGCAGAGGCCGAGGCCGCCTCTGCC

TCTGAGCTATTCCAGAAGTAGTGAGGAGGCTTTTTTGGAGGCCTAGGCTTTTGCAAAAAGCTCCCGGGAGCTTGTAT

ATCCATTTTCGGATCTGATCAAGAGACAGGATGAGGATCGTTTCGCATGATTGAACAAGATGGATTGCACGCAGGTT

CTCCGGCCGCTTGGGTGGAGAGGCTATTCGGCTATGACTGGGCACAACAGACAATCGGCTGCTCTGATGCCGCCGTG
```

-continued

```
TTCCGGCTGTCAGCGCAGGGGCGCCCGGTTCTTTTTGTCAAGACCGACCTGTCCGGTGCCCTGAATGAACTGCAGGA
CGAGGCAGCGCGGCTATCGTGGCTGGCCACGACGGGCGTTCCTTGCGCAGCTGTGCTCGACGTTGTCACTGAAGCGG
GAAGGGACTGGCTGCTATTGGGCGAAGTGCCGGGGCAGGATCTCCTGTCATCTCACCTTGCTCCTGCCGAGAAAGTA
TCCATCATGGCTGATGCAATGCGGCGGCTGCATACGCTTGATCCGGCTACCTGCCCATTCGACCACCAAGCGAAACA
TCGCATCGAGCGAGCACGTACTCGGATGGAAGCCGGTCTTGTCGATCAGGATGATCTGGACGAAGAGCATCAGGGGC
TCGCGCCAGCCGAACTGTTCGCCAGGCTCAAGGCGCGCATGCCCGACGGCGAGGATCTCGTCGTGACCCATGGCGAT
GCCTGCTTGCCGAATATCATGGTGGAAAATGGCCGCTTTTCTGGATTCATCGACTGTGGCCGGCTGGGTGTGGCGGA
CCGCTATCAGGACATAGCGTTGGCTACCCGTGATATTGCTGAAGAGCTTGGCGGCGAATGGGCTGACCGCTTCCTCG
TGCTTTACGGTATCGCCGCTCCCGATTCGCAGCGCATCGCCTTCTATCGCCTTCTTGACGAGTTCTTCTGAGCGGGA
CTCTGGGGTTCGAAATGACCGACCAAGCGACGCCCAACCTGCCATCACGAGATTTCGATTCCACCGCCGCCTTCTAT
GAAAGGTTGGGCTTCGGAATCGTTTTCCGGGACGCCGGCTGGATGATCCTCCAGCGCGGGATCTCATGCTGGAGTT
CTTCGCCCACCCCAACTTGTTTATTGCAGCTTATAATGGTTACAAATAAAGCAATAGCATCACAAATTTCACAAATA
AAGCATTTTTTTCACTGCATTCTAGTTGTGGTTTGTCCAAACTCATCAATGTATCTTATCATGTCTGTATACATGTG
AGCAAAAGGCCAGCAAAAGGCCAGGAACCGTAAAAAGGCCGCGTTGCTGGCGTTTTTCCATAGGCTCCGCCCCCCTG
ACGAGCATCACAAAAATCGACGCTCAAGTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGGATACCTGTCCGCCTTTCTCCCTTCGGG
AAGCGTGGCGCTTTCTCAATGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAACCCGGTAAGACAC
GACTTATCGCCACTGGCAGCAGCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCTGCTGAAGCCAGTTACCTTCG
GAAAAAGAGTTGGTAGCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGCTCAGTGGAACGAAAA
CTCACGTTAAGGGATTTTGGTCATGAGATTATCAAAAAGGATCTTCACCTAGATCCTTTTAAATTAAAAATGAAGTT
TTAAATCAATCTAAAGTATATATGAGTAAACTTGGTCTGACAGTTACCAATGCTTAATCAGTGAGGCACCTATCTCA
GCGATCTGTCTATTTCGTTCATCCATAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACATGATCCCCCATGTTGTGCAAAAAAG
CGGTTAGCTCCTTCGGTCCTCCGATCGTTGTCAGAAGTAAGTTGGCCGCAGTGTTATCACTCATGGTTATGGCAGCA
CTGCATAATTCTCTTACTGTCATGCCATCCGTAAGATGCTTTTCTGTGACTGGTGAGTACTCAACCAAGTCATTCTG
AGAATAGTGTATGCGGCGACCGAGTTGCTCTTGCCCGGCGTCAATACGGGATAATACCGCGCCACATAGCAGAACTT
TAAAAGTGCTCATCATTGGAAAACGTTCTTCGGGGCGAAAACTCTCAAGGATCTTACCGCTGTTGAGATCCAGTTCG
ATGTAACCCACTCGTGCACCCAACTGATCTTCAGCATCTTTTACTTTCACCAGCGTTTCTGGGTGAGCAAAAACAGG
AAGGCAAAATGCCGCAAAAAAGGGAATAAGGGCGACACGGAAATGTTGAATACTCATACTCTTCCTTTTTCAATATT
ATTGAAGCATTTATCAGGGTTATTGTCTCATGAGCGGATACATATTTGAATGTATTTAGAAAAATAAACAAATAGGG
GTTCCGCGCACATTTCCCCGAAAAGTGCCACCTGACGTCTAAGAAACCATTATTATCATGACATTAACCTATAAAAA
TAGGCGTATCACGAGGCCCCTTTCGTCTCGCGCGTTTCGGTGATGACGGTGAAAACCTCTGACACATGCAGCTCCCG
GAGACGGTCACAGCTTGTCTGTAAGCGGATGCCGGGAGCAGACAAGCCCGTCAGGGCGCGTCAGCGGGTGTTGGCGG
GTGTCGGGGCTGGCTTAACTATGCGGCATCAGAGCAGATTGTACTGAGAGTGCACCATATGCGGTGTGAAATACCGC
```

-continued
```
ACAGATGCGTAAGGAGAAAATACCGCATCAGGAAATTGTAAACGTTAATATTTTGTTAAAATTCGCGTTAAATTTTT

GTTAAATCAGCTCATTTTTTAACCAATAGGCCGAAATCGGCAAAATCCCTTATAAATCAAAAGAATAGACCGAGATA

GGGTTGAGTGTTGTTCCAGTTTGGAACAAGAGTCCACTATTAAAGAACGTGGACTCCAACGTCAAAGGGCGAAAAAC

CGTCTATCAGGGCGATGGCCCACTACGTGATCTGGCCTCCGCGCCGGGTTTTGGCGCCCCCCGCGGGCGCCCCCCTC

CTCACGGCGAGCGCTGCCACGTCAGACGAAGGGCGCAGCGAGCGTCCTGATCCTTCCGCCCGGACGCTCAGGACAGC

GGCCCGCTGCTCATAAGACTCGGCCTTAGAACCCCAGTATCAGCAGAAGGACATTTTAGGACGGGACTTGGGTGACT

CTAGGGCACTGGTTTTCTTTCCAGAGAGCGGAACAGGCGAGGAAAAGTAGTCCCTTCTCGGCGATTCTGCGGAGGGA

TCTCCGTGGGGCGGTGAACGCCGATGATTATATAAGGACGCGCCGGGTGTGGCACAGCTAGTTCCGTCGCAGCCGGG

ATTTGGGTCGCGGTTCTTGTTTGTGGATCGCTGTGATCGTCACTTGGTGAGTAGCGGGCTGCTGGGCTGGCCGGGGC

TTTCGTGGCCGCCGGGCCGCTCGGTGGGACGGAAGCGTGTGGAGAGACCGCCAAGGGCTGTAGTCTGGGTCCGCGAG

CAAGGTTGCCCTGAACTGGGGGTTGGGGGGAGCGCAGCAAAATGGCGGCTGTTCCCGAGTCTTGAATGGAAGACGCT

TGTGAGGCGGGCTGTGAGGTCGTTGAAACAAGGTGGGGGGCATGGTGGGCGGCAAGAACCCAAGGTCTTGAGGCCTT

CGCTAATGCGGGAAAGCTCTTATTCGGGTGAGATGGGCTGGGGCACCATCTGGGGACCCTGACGTGAAGTTTGTCAC

TGACTGGAGAACTCGGTTTGTCGTCTGTTGCGGGGGCGGCAGTTATGGCGGTGCCGTTGGGCAGTGCACCCGTACCT

TTGGGAGCGCGCGCCCTCGTCGTGTCGTGACGTCACCCGTTCTGTTGGCTTATAATGCAGGGTGGGGCCACCTGCCG

GTAGGTGTGCGGTAGGCTTTTCTCCGTCGCAGGACGCAGGGTTCGGGCCTAGGGTAGGCTCTCCTGAATCGACAGGC

GCCGGACCTCTGGTGAGGGGAGGGATAAGTGAGGCGTCAGTTTCTTTGGTCGGTTTTATGTACCTATCTTCTTAAGT

AGCTGAAGCTCCGGTTTTGAACTATGCGCTCGGGGTTGGCGAGTGTGTTTTGTGAAGTTTTTTAGGCACCTTTTGAA

ATGTAATCATTTGGGTCAATATGTAATTTTCAGTGTTAGACTAGTAAATTGTCCGCTAAATTCTGGCCGTTTTTGGC

TTTTTTGTTAGACCGGACCG
```

A human cell line (HEK293F) has been chosen for its ability to grow in suspension and in a serum and protein free medium (Florian M Wurm "Production of recombinant protein therapeutics in cultivated mammalian cells" Nature Biotechnology 22(11):1393-1398, 2004, Yan S C et al. "Characterization and novel purification of recombinant human protein C from three mammalian cell lines" Biotechnology (N.Y.) 1990 Jul. 8 (7): 655-61. "Use of cell lines for the production of influenza virus vaccines: an appraisal of technical, manufacturing, and regulatory considerations" Initiative for Vaccine Research, World Health Organization, Geneva, Switzerland (10 Apr. 2007). To transfect HEK293F, pSC1-PTX3 plasmid was used either in a linear (PvuI digested) or in a circular form. The best transfection yield was obtained with linearized plasmid; clones selection was done on a productivity base and growth capability. After several rounds of subcloning the 2F12 clone was selected.

The human clone 2F12, expressing hPTX3, has been deposited at ECACC (European Collection of Cell Cultures, Health Protection Agency, Porton Down, Wiltshire SP4 0JG, UK) on Jan. 10, 2008, pursuant to Budapest Treaty condition under deposit number 08011001. The experimental details are described below.

3.4 Recombinant 293F-Cells Generated from pSC1-PTX3 Transfection and Subcloning

10⁶ cells/ml 293F (Invitrogen cat n° R790-07) were seeded in a 125ml spinner flask in a final FREESTYLE™ medium volume of 28ml the day of transfection. The pSC1/PTX3plasmid was then allowed to adsorb to the 293FECTIN™ reagent (GIBCO/Invitrogen) according to the manufacturer's protocol.

In brief, in two separate tubes, 30 μg of pSC1-PTX3circular or PvuI linearized were diluted in 1ml of OPTI-MEM® (GIBCO/Invitrogen, Carlsbad, CA, USA) and 40 μl of 293FECTIN™ (Invitrogen) diluted to 1ml with OPTI-MEM®. Both solutions were incubated for 5minutes at room temperature then mixed (final volume 2ml) and incubated for 30minutes in the same conditions. DNA/lipid cocktail was added to cells and incubated at 37° C., 5% CO2with agitation (120rpm). After cultivation for 36hours, the medium was changed into selection medium (200ml FREESTYLE™ medium+500 μg/ml of G418) and the transfected cells were plated in ten 96wells plates, 200 μl/well. After 15 days highest producers cell-pools were determined by ELISA and amplified in 24wells, 6wells and T25flask.

Recombinant cell-pools obtained were subcloned with 1 cells per well in 96wells plates, in 50% fresh medium and 50% conditioned medium.

Example 2

Clone MS24PTX

Construction of the plasmid pSASSI-hPTX3
  1. Construction of pCEPlightΔ
  pCEP4 plasmid (Invitrogen cat. n. V044-50), in which was previously cloned an antibody light chain, loosing a portion of the Multiple Cloning Site and the BamHI restriction site, was cut with the restriction enzymes EcoRV and ClaI (Roche Applied Science); the digestion allowed to obtain a plasmid without the Epstein-Barr-Virus replication origin (oriP) and the nuclear antigen (encoded by the EBNA-1 gene) that permit extrachromosomal replication. The resulting fragments were 6910 and 4281 bp long. The 6910 bp fragment, containing the backbone of pCEP, was purified via agarose gel electrophoresis plus silica membrane spin column. Since ClaI generates sticky end, the fragment was filled in, using T4 DNA polymerase (Roche Applied Science) with the follow protocol: 150 ng of ClaI/EcoRV purified fragment (38 µl), 5 µl of 10× T4 DNA polymerase buffer, 4 µl of dNTP mix 2.5 mM, 3 µl of T4 DNA polymerase (1U/µl). After 15 minutes at 37° C., the reaction was stopped at 70° C. for 5 minutes then on ice. The fragment was purified on a silica membrane spin column and ligated on itself over night at room temperature, by using T4 DNA ligase (Promega). TOP10 competent cells (Invitrogen) were transformed with the ligation mixture and transformants selected by growth on LB plates supplemented with 100 mg/L ampicillin.

Plasmid DNA, isolated from ampicillin resistant colonies, was designed as pCEPlightΔ.

2. Preparation of Vector Fragment Containing Hygromycin Resistance and CMV Promoter.

The Hygromycin Resistance Cassette together with the cytomegalovirus (CMV) immediate early enhancer/promoter was taken from pCEPlightΔ amplifying it by PCR. As a part of the cloning strategy, recognition sequence for restriction endonuclease BamHI was introduced in the oligonucleotide annealing to the 3' end of CMV promoter.

The amplified region about 5500 bp, included CMV promoter, Hygromycin gene under the control of TK promoter together with TK polyA signal.

The oligonucleotide are designed as follows:

```
oligo CMV
                                      (SEQ ID NO: 9)
5'GAGAACTGTAACGTTGGATCCAGCTGG 3' oligo H
                                     (SEQ ID NO: 10)
5'GTGTACAAAGGATCCAGACATGATAAG 3'
```

Protocol for amplification was the following: 2 ng of pCEPlightΔ, 200 nM of each primer, 0.2 mM dNTPs, 1× supplied buffer, 1.5 µl DMSO, 0.5 µl Taq DNA polymerase (Phusion), final volume 50 µl; temperature profile: 1 min 98° C., 35 times (10 sec. 98° C., 30 sec. 55° C., 3 min. 72° C.), 10 min. 72° C., cooling at 4° C. until further use.

The amplification product (~5500 bp) was purified via agarose gel electrophoresis plus silica membrane spin column. Purified fragment was ligated to itself and use to transform TOP10 competent cells (Invitrogen). Plasmid DNA, isolated from ampicillin resistant colonies, was checked by restriction and sequence analysis. and was designed as pCEPΔBam.

3. Preparation of hPTX3 Gene

The hPTX3(GENBANK® Accession Number BD 131701) sequence was taken from pSC1-PTX3as indicated above by BamHI (Roche Applied Science) digestion. Human PTX3fragment (1463bp) was purified by agarose gel electrophoresis and silica membrane spin column.

4. Preparation of pCEPΔBam-hPTX3

The pCEPΔBam vector was linearized by BamHI digestion and purified on silica membrane spin column. pCEPΔBam linearized and DNA fragment corresponding to hPTX3 gene prepared in step 3 were ligated using T4 DNA ligase (Roche Applied Science) and used to transform TOP10 E. coli strain. Transformants were selected by growth on LB medium, supplemented with 100 mg/L ampicillin and preliminarily screened restriction analysis to evaluate PTX3 fragment orientation.

5. Preparation of SV40 Polyadenilation Signal

The SV40 polyA signal was taken from pCEPΔlight plasmid amplifying it by PCR. As part of the cloning strategy, recognition sequences for restriction endonucleoases HindIII and XhoI were introduced at fragment ends respectively.

The oligonucleotides were designed as follows:

```
PCEPSVH
                                     (SEQ ID NO: 11)
5'AAGCTTAGACATGATAAGATACATTG 3'

PCEPSVX
                                     (SEQ ID NO: 12)
5'CTCGAGAGTCGACCGGTCATGGCTGC 3'
```

Protocol for amplification was the following: 1 ng of pCEPlightΔ, 200 nM of each primer, 0.2 mM dNTPs, 1× supplied buffer, 2 µl MgCl2 50 mM, 0.5 µl Taq DNA polymerase (Invitrogen), final volume 50 µl; temperature profile: 1 min 94° C., 30 times (30 sec. 94° C., 1 min. 55° C., 1 min. 72° C.), 15 min. 72° C., cooling at 4° C. until further use.

The amplification product (~420 bp) was purified via agarose gel electrophoresis plus silica membrane spin column.

6. Preparation of pSASSI-hPTX3 Purified fragment corresponding to SV40 polyA signal and pCEPΔBam-hPTX3 were digested with HindIII/XhoI restriction enzymes and ligated using T4 DNA ligase (Promega). Ligation mixture was used to transform TOP10 competent cells (Invitrogen) and transformants were selected by growth on LB plates containing 100 mg/L of ampicillin.

Plasmid DNA isolated from ampicillin resistant colonies, was checked by restriction and sequence analysis and the plasmid was designated pSASSI-hPTX3.

The complete sequence of pSASSI-HPTX3is as follows (SEQ ID NO: 1). The pSASSI-hPTX 3sequence is represented starting from the BamHI site (FIG. 1). The sequence of hPTX3is in small letters. The starting codon (atg) and the termination codon (taa) are in bold.

pSASSI-HPTX3 (SEQ ID NO: 1)

```
pSASSI-HPTX3.
                                                                    (SEQ ID NO: 1)
        GGATCCCCCG GGCTGCAGGA ATTCCGGCTC AAACTCAGCT CACTTGAGAG TCTCCTCCCG    60

CCAGCTGTGG AAAGAACTTT GCGTCTCTCC AGCAATGCAT CTCCTTGCGA TTCTGTTTTG   120

TGCTCTCTGG TCTGCAGTGT TGGCCGAGAA CTCGGATGAT TATGATCTCA TGTATGTGAA   180

TTTGGACAAC GAAATAGACA ATGGACTCCA TCCCACTGAG GACCCCACGC CGTGCGACTG   240

CGGTCAGGAG CACTCGGAAT GGGACAAGCT CTTCATCATG CTGGAGAACT CGCAGATGAG   300

AGAGCGCATG CTGCTGCAAG CCACGGACGA CGTCCTGCGG GGCGAGCTGC AGAGGCTGCG   360

GGAGGAGCTG GGCCGGCTCG CGGAAAGCCT GGCGAGGCCG TGCGCGCCGG GGGCTCCCGC   420

AGAGGCCAGG CTGACCAGTG CTCTGGACGA GCTGCTGCAG GCGACCCGCG ACGCGGGCCG   480
```

```
                                       -continued
CAGGCTGGCG CGTATGGAGG GCGCGGAGGC GCAGCGCCCA GAGGAGGCGG GGCGCGCCCT      540

GGCCGCGGTG CTAGAGGAGC TGCGGCAGAC GCGAGCCGAC CTGCACGCGG TGCAGGGCTG      600

GGCTGCCCGG AGCTGGCTGC CGGCAGGTTG TGAAACAGCT ATTTTATTCC CAATGCGTTC      660

CAAGAAGATT TTTGGAAGCG TGCATCCAGT GAGACCAATG AGGCTTGAGT CTTTTAGTGC      720

CTGCATTTGG GTCAAAGCCA CAGATGTATT AAACAAAACC ATCCTGTTTT CCTATGGCAC      780

AAAGAGGAAT CCATATGAAA TCCAGCTGTA TCTCAGCTAC CAATCCATAG TGTTTGTGGT      840

GGGTGGAGAG GAGAACAAAC TGGTTGCTGA AGCCATGGTT TCCCTGGGAA GGTGGACCCA      900

CCTGTGCGGC ACCTGGAATT CAGAGGAAGG GCTCACATCC TTGTGGGTAA ATGGTGAACT      960

GGCGGCTACC ACTGTTGAGA TGGCCACAGG TCACATTGTT CCTGAGGGAG GAATCCTGCA     1020

GATTGGCCAA GAAAAGAATG GCTGCTGTGT GGGTGGTGGC TTTGATGAAA CATTAGCCTT     1080

CTCTGGGAGA CTCACAGGCT TCAATATCTG GATAGTGTT CTTAGCAATG AAGAGATAAG     1140

AGAGACCGGA GGAGCAGAGT CTTGTCACAT CCGGGGGAAT ATTGTTGGGT GGGGAGTCAC     1200

AGAGATCCAG CCACATGGAG GAGCTCAGTA TGTTTCATAA ATGTTGTGAA ACTCCACTTG     1260

AAGCCAAAGA AAGAAACTCA CACTTAAAAC ACATGCCAGT TGGGAAGGTC TGAAAACTCA     1320

GTGCATAATA GGAACACTTG AGACTAATGA AAGAGAGAGT TGAGACCAAT CTTTATTTGT     1380

ACTGGCCAAA TACTGAATAA ACAGTTGAAG GAAAGACATT GGAAAAAGCT TAGACATGAT     1440

AAGATACATT GATGAGTTTG ACAAACCAC AACTAGAATG CAGTGAAAAA AATGCTTTAT     1500

TTGTGAAATT TGTGATGCTA TTGCTTTATT TGTAACCATT ATAAGCTGCA ATAAACAAGT     1560

TAACAACAAC AATTGCATTC ATTTTATGTT TCAGGTTCAG GGGGAGGTGT GGGAGGTTTT     1620

TTAAAGCAAG TAAAACCTCT ACAAATGTGG TATGGCTGAT TATGATCCGG CTGCCTCGCG     1680

CGTTTCGGTG ATGACGGTGA AAACCTCTGA CACATGCAGC TCCCGGAGAC GGTCACAGCT     1740

TGTCTGTAAG CGGATGCCGG GAGCAGACAA GCCCGTCAGG GCGCGTCAGC GGGTGTTGGC     1800

GGGTGTCGGG GCGCAGCCAT GACCGGTCGA CTCTCGAGGG GGGGCCCGGG GATCCAACGT     1860

TACAGTTCTC CAGTGCATGT AATCCCTTCA GTTGGTTGGT ACAACTTGCC AACTGGGCCC     1920

TGTTCCACAT GTGACACGGG GGGGGACCAA ACACAAAGGG GTTCTCTGAC TGTAGTTGAC     1980

ATCCTTATAA ATGGATGTGC ACATTTGCCA ACACTGAGTG GCTTTCATCC TGGAGCAGAC     2040

TTTGCAGTCT GTGGACTGCA ACACAACATT GCCTTTATGT GTAACTCTTG GCTGAAGCTC     2100

TTACACCAAT GCTGGGGGAC ATGTACCTCC CAGGGGCCCA GGAAGACTAC GGGAGGCTAC     2160

ACCAACGTCA ATCAGAGGGG CCTGTGTAGC TACCGATAAG CGGACCCTCA AGAGGGCATT     2220

AGCAATAGTG TTTATAAGGC CCCCTTGTTA ACCCTAAACG GGTAGCATAT GCTTCCCGGG     2280

TAGTAGTATA TACTATCCAG ACTAACCCTA ATTCAATAGC ATATGTTACC CAACGGGAAG     2340

CATATGCTAT CGAATTAGGG TTAGTAAAAG GGTCCTAAGG AACAGCGATC GATGATAAGC     2400

TGTCAAACAT GAGAATTCTT GAAGACGAAA GGGCCTCGTG ATACGCCTAT TTTTATAGGT     2460

TAATGTCATG ATAATAATGG TTTCTTAGAC GTCAGGTGGC ACTTTCGGG GAAATGTGCG     2520

CGGAACCCCT ATTTGTTTAT TTTTCTAAAT ACATTCAAAT ATGTATCCGC TCATGAGACA     2580

ATAACCCTGA TAAATGCTTC AATAATATTG AAAAGGAAG AGTATGAGTA TTCAACATTT     2640

CCGTGTCGCC CTTATTCCCT TTTTTGCGGC ATTTTGCCTT CCTGTTTTTG CTCACCCAGA     2700

AACGCTGGTG AAAGTAAAAG ATGCTGAAGA TCAGTTGGGT GCACGAGTGG GTTACATCGA     2760

ACTGGATCTC AACAGCGGTA AGATCCTTGA GAGTTTTCGC CCCGAAGAAC GTTTTCCAAT     2820

GATGAGCACT TTTAAAGTTC TGCTATGTGG CGCGGTATTA TCCCGTGTTG ACGCCGGGCA     2880
```

-continued

```
AGAGCAACTC GGTCGCCGCA TACACTATTC TCAGAATGAC TTGGTTGAGT ACTCACCAGT    2940

CACAGAAAAG CATCTTACGG ATGGCATGAC AGTAAGAGAA TTATGCAGTG CTGCCATAAC    3000

CATGAGTGAT AACACTGCGG CCAACTTACT TCTGACAACG ATCGGAGGAC CGAAGGAGCT    3060

AACCGCTTTT TTGCACAACA TGGGGGATCA TGTAACTCGC CTTGATCGTT GGGAACCGGA    3120

GCTGAATGAA GCCATACCAA ACGACGAGCG TGACACCACG ATGCCTGCAG CAATGGCAAC    3180

AACGTTGCGC AAACTATTAA CTGGCGAACT ACTTACTCTA GCTTCCCGGC AACAATTAAT    3240

AGACTGGATG GAGGCGGATA AAGTTGCAGG ACCACTTCTG CGCTCGGCCC TTCCGGCTGG    3300

CTGGTTTATT GCTGATAAAT CTGGAGCCGG TGAGCGTGGG TCTCGCGGTA TCATTGCAGC    3360

ACTGGGGCCA GATGGTAAGC CCTCCCGTAT CGTAGTTATC TACACGACGG GGAGTCAGGC    3420

AACTATGGAT GAACGAAATA GACAGATCGC TGAGATAGGT GCCTCACTGA TTAAGCATTG    3480

GTAACTGTCA GACCAAGTTT ACTCATATAT ACTTTAGATT GATTTAAAAC TTCATTTTTA    3540

ATTTAAAAGG ATCTAGGTGA AGATCCTTTT TGATAATCTC ATGACCAAAA TCCCTTAACG    3600

TGAGTTTTCG TTCCACTGAG CGTCAGACCC CGTAGAAAAG ATCAAAGGAT CTTCTTGAGA    3660

TCCTTTTTTT CTGCGCGTAA TCTGCTGCTT GCAAACAAAA AAACCACCGC TACCAGCGGT    3720

GGTTTGTTTG CCGGATCAAG AGCTACCAAC TCTTTTTCCG AAGGTAACTG GCTTCAGCAG    3780

AGCGCAGATA CCAAATACTG TCCTTCTAGT GTAGCCGTAG TTAGGCCACC ACTTCAAGAA    3840

CTCTGTAGCA CCGCCTACAT ACCTCGCTCT GCTAATCCTG TTACCAGTGG CTGCTGCCAG    3900

TGGCGATAAG TCGTGTCTTA CCGGGTTGGA CTCAAGACGA TAGTTACCGG ATAAGGCGCA    3960

GCGGTCGGGC TGAACGGGGG GTTCGTGCAC ACAGCCCAGC TTGGAGCGAA CGACCTACAC    4020

CGAACTGAGA TACCTACAGC GTGAGCTATG AGAAAGCGCC ACGCTTCCCG AAGGGAGAAA    4080

GGCGGACAGG TATCCGGTAA GCGGCAGGGT CGGAACAGGA GAGCGCACGA GGGAGCTTCC    4140

AGGGGGAAAC GCCTGGTATC TTTATAGTCC TGTCGGGTTT CGCCACCTCT GACTTGAGCG    4200

TCGATTTTTG TGATGCTCGT CAGGGGGGCG GAGCCTATGG AAAAACGCCA GCAACGCGGC    4260

CTTTTTACGG TTCCTGGCCT TTTGCTGCGC CGCGTGCGGC TGCTGGAGAT GGCGGACGCG    4320

ATGGATATGT TCTGCCAAGG GTTGGTTTGC GCATTCACAG TTCTCCGCAA GAATTGATTG    4380

GCTCCAATTC TTGGAGTGGT GAATCCGTTA GCGAGGTGCC GCCGGCTTCC ATTCAGGTCG    4440

AGGTGGCCCG GCTCCATGCA CCGCGACGCA ACGCGGGGAG GCAGACAAGG TATAGGGCGG    4500

CGCCTACAAT CCATGCCAAC CCGTTCCATG TGCTCGCCGA GGCGGCATAA ATCGCCGTGA    4560

CGATCAGCGG TCCAGTGATC GAAGTTAGGC TGGTAAGAGC CGCGAGCGAT CCTTGAAGCT    4620

GTCCCTGATG GTCGTCATCT ACCTGCCTGG ACAGCATGGC CTGCAACGCG GGCATCCCGA    4680

TGCCGCCGGA AGCGAGAAGA ATCATAATGG GGAAGGCCAT CCAGCCTCGC GTCGCGAACG    4740

GCGAACGCCA GCAAGACGTA GCCCAGCGCG TCGGCCGCCA TGCCCTGCTT CATCCCCGTG    4800

GCCCGTTGCT CGCGTTTGCT GGCGGTGTCC CCGGAAGAAA TATATTTGCA TGTCTTTAGT    4860

TCTATGATGA CACAAACCCC GCCCAGCGTC TTGTCATTGG CGAATTCGAA CACGCAGATG    4920

CAGTCGGGGC GGCGCGGTCC CAGGTCCACT TCGCATATTA AGGTGACGCG TGTGGCCTCG    4980

AACACCGAGC GACCCTGCAG CGACCCGCTT AACAGCGTCA ACAGCGTGCC GCAGATCCCG    5040

GGCAATGAGA TATGAAAAAG CCTGAACTCA CCGCGACGTC TGTCGAGAAG TTTCTGATCG    5100

AAAAGTTCGA CAGCGTCTCC GACCTGATGC AGCTCTCGGA GGGCGAAGAA TCTCGTGCTT    5160

TCAGCTTCGA TGTAGGAGGG CGTGGATATG TCCTGCGGGT AAATAGCTGC GCCGATGGTT    5220

TCTACAAAGA TCGTTATGTT TATCGGCACT TTGCATCGGC CGCGCTCCCG ATTCCGGAAG    5280

TGCTTGACAT TGGGGAATTC AGCGAGAGCC TGACCTATTG CATCTCCCGC CGTGCACAGG    5340
```

```
GTGTCACGTT GCAAGACCTG CCTGAAACCG AACTGCCCGC TGTTCTGCAG CCGGTCGCGG      5400

AGGCCATGGA TGCGATCGCT GCGGCCGATC TTAGCCAGAC GAGCGGGTTC GGCCCATTCG      5460

GACCGCAAGG AATCGGTCAA TACACTACAT GGCGTGATTT CATATGCGCG ATTGCTGATC      5520

CCCATGTGTA TCACTGGCAA ACTGTGATGG ACGACACCGT CAGTGCGTCC GTCGCGCAGG      5580

CTCTCGATGA GCTGATGCTT TGGGCCGAGG ACTGCCCCGA AGTCCGGCAC CTCGTGCACG      5640

CGGATTTCGG CTCCAACAAT GTCCTGACGG ACAATGGCCG CATAACAGCG GTCATTGACT      5700

GGAGCGAGGC GATGTTCGGG GATTCCCAAT ACGAGGTCGC CAACATCTTC TTCTGGAGGC      5760

CGTGGTTGGC TTGTATGGAG CAGCAGACGC GCTACTTCGA GCGGAGGCAT CCGGAGCTTG      5820

CAGGATCGCC GCGGCTCCGG GCGTATATGC TCCGCATTGG TCTTGACCAA CTCTATCAGA      5880

GCTTGGTTGA CGGCAATTTC GATGATGCAG CTTGGGCGCA GGGTCGATGC GACGCAATCG      5940

TCCGATCCGG AGCCGGGACT GTCGGGCGTA CACAAATCGC CCGCAGAAGC GCGGCCGTCT      6000

GGACCGATGG CTGTGTAGAA GTACTCGCCG ATAGTGGAAA CCGACGCCCC AGCACTCGTC      6060

CGAGGGCAAA GGAATAGGGG AGATGGGGGA GGCTAACTGA AACACGGAAG GAGACAATAC      6120

CGGAAGGAAC CCGCGCTATG ACGGCAATAA AAAGACAGAA TAAAACGCAC GGGTGTTGGG      6180

TCGTTTGTTC ATAAACGCGG GGTTCGGTCC CAGGGCTGGC ACTCTGTCGA TACCCCACCG      6240

AGACCCCATT GGGGCCAATA CGCCCGCGTT TCTTCCTTTT CCCCACCCCA CCCCCCAAGT      6300

TCGGGTGAAG GCCCAGGGCT CGCAGCCAAC GTCGGGCGG CAGGCCCTGC CATAGCCACT       6360

GGCCCCGTGG GTTAGGGACG GGGTCCCCCA TGGGGAATGG TTTATGGTTC GTGGGGGTTA      6420

TTATTTTGGG CGTTGCGTGG GGTCTGGTCC ACGACTGGAC TGAGCAGACA GACCCATGGT      6480

TTTTGGATGG CCTGGGCATG GACCGCATGT ACTGGCGCGA CACGAACACC GGGCGTCTGT      6540

GGCTGCCAAA CACCCCCGAC CCCCAAAAAC CACCGCGCGG ATTTCTGGCG TGCCAAGCTA      6600

GTCGACCAAT TCTCATGTTT GACAGCTTAT CATCGCAGAT CCGGGCAACG TTGTTGCCAT      6660

TGCTGCAGGC GCAGAACTGG TAGGTATGGA AGATCTATAC ATTGAATCAA TATTGGCAAT      6720

TAGCCATATT AGTCATTGGT TATATAGCAT AAATCAATAT TGGCTATTGG CCATTGCATA      6780

CGTTGTATCT ATATCATAAT ATGTACATTT ATATTGGCTC ATGTCCAATA TGACCGCCAT      6840

GTTGACATTG ATTATTGACT AGTTATTAAT AGTAATCAAT TACGGGGTCA TTAGTTCATA      6900

GCCCATATAT GGAGTTCCGC GTTACATAAC TTACGGTAAA TGGCCCGCCT GGCTGACCGC      6960

CCAACGACCC CCGCCCATTG ACGTCAATAA TGACGTATGT TCCCATAGTA ACGCCAATAG      7020

GGACTTTCCA TTGACGTCAA TGGGTGGAGT ATTTACGGTA AACTGCCCAC TTGGCAGTAC      7080

ATCAAGTGTA TCATATGCCA AGTCCGCCCC CTATTGACGT CAATGACGGT AAATGGCCCG      7140

CCTGGCATTA TGCCCAGTAC ATGACCTTAC GGGACTTTCC TACTTGGCAG TACATCTACG      7200

TATTAGTCAT CGCTATTACC ATGGTGATGC GGTTTTGGCA GTACACCAAT GGGCGTGGAT      7260

AGCGGTTTGA CTCACGGGGA TTTCCAAGTC TCCACCCCAT TGACGTCAAT GGGAGTTTGT      7320

TTTGGCACCA AAATCAACGG GACTTTCCAA AATGTCGTAA TAACCCCGCC CCGTTGACGC      7380

AAATGGGCGG TAGGCGTGTA CGGTGGGAGG TCTATATAAG CAGAGCTCGT TTAGTGAACC      7440

GTCAGATCTC TAGAAGCTGG GTACCAGCT                                       7469
```

Example 3

Recombinant Ms24PTX Clone Generated by pSASSI-hPTX3 Transfection

1. Transfection and Subcloning $10^6$ cells/ml 293F/PTX3/2F12were seeded in a 125ml spinner flask in a final FREESTYLE™ medium volume of 28 ml the day of transfection. The pSASSI-hPTX3 plasmid was then allowed to adsorb to the 293FECTIN™ reagent (GIBCO/Invitrogen) according to the manufacturer's protocol.

In brief, 30 µg of pSASSI-hPTX3NruI linearized was diluted in 1ml of OPTIMEN ® (GIBCO/Invitrogen, Carlsbad, CA, USA) and 40 µl of 293FECTIN™ (Invitrogen) diluted to 1ml with OPTIMEN ®. Both solutions were incubated for 5minutes at room temperature then mixed (final volume 2ml) and incubated for 30 minutes in the same conditions. DNA/lipid cocktail was added to cells and incubated at 37° C., 5% $CO_2$ with agitation 120rpm). After cultivation for 36hours, the medium was changed into selection medium (200ml FREESTYLE™ medium+200 µg/ml of Hygromycin) and the transfected cells were plated in ten 96wells plates, 200 µl/well. After 15days highest producers cell-pools were determined by ELISA and amplified in 24wells, 6wells and T25flask.

Recombinant cell-pools obtained were subcloned with 1 cells per well in 96wells plates, in 50% fresh medium and 50% conditioned medium.

2. ELISA Detection of Recombinant hPTX3

Purified PTX3or PTX3secreted in the culture supernatant were titrated using a sandwich ELISA. To detect PTX3, 96-well Nunc MAXISORB® microtiter plates (Nunc, Roskilde, Denmark) were coated overnight, at 4° C., with 700ng/ml of the rat monoclonal antibody MNB4anti-human PTX3 (Alexis™ Biochemicals, Lausen, Switzerland) in 15 mM sodium carbonate buffer, pH 9.6. Wells were washed with PBS plus 0.05% TWEEN®-20 (PBS-Tw, washing solution) and blocked with 300 µl of PBS-Tw containing 5% dry milk, for 2hours at room temperature.

Cell supernatants or purified recombinant human PTX3 were added to the wells, diluted in washing solution plus 1% BSA. A standard curve, made with purified recombinant human PTX3 from CHO cells, ranging from 0 to 100 ng/ml, was done for quantification. After 1 hour of incubation at 37° C., bound PTX3 was detected using biotin-conjugated polyclonal rabbit anti-PTX 3 antibody, followed by incubation with streptavidin conjugated to horseradish peroxidase (Sigma-Aldrich, USA). Finally 2.2'-azino-bis 3-ethyl-benxthiazoline-6-sulfonic acid (Sigma Chemical Co. USA) was added for color development and optical density at 405 nm was assessed using a Microplate Reader Model 3550 EIA (Bio-Rad, Hercules, Calif., USA).

Example 4

Comparison of Growth, Viability and Productivity of Clones 293F/PTX3/2F12 and MS24PTX Cells deriving from the two clones were seeded at a density of 1.000.000cells/ml (viability ≥90%) in a 500ml of FREESTYLE™ 293medium in 1liter Spinner flasks. The growing, the viability and the productivity were monitored for about 1week until cells start die.

Figure 2:
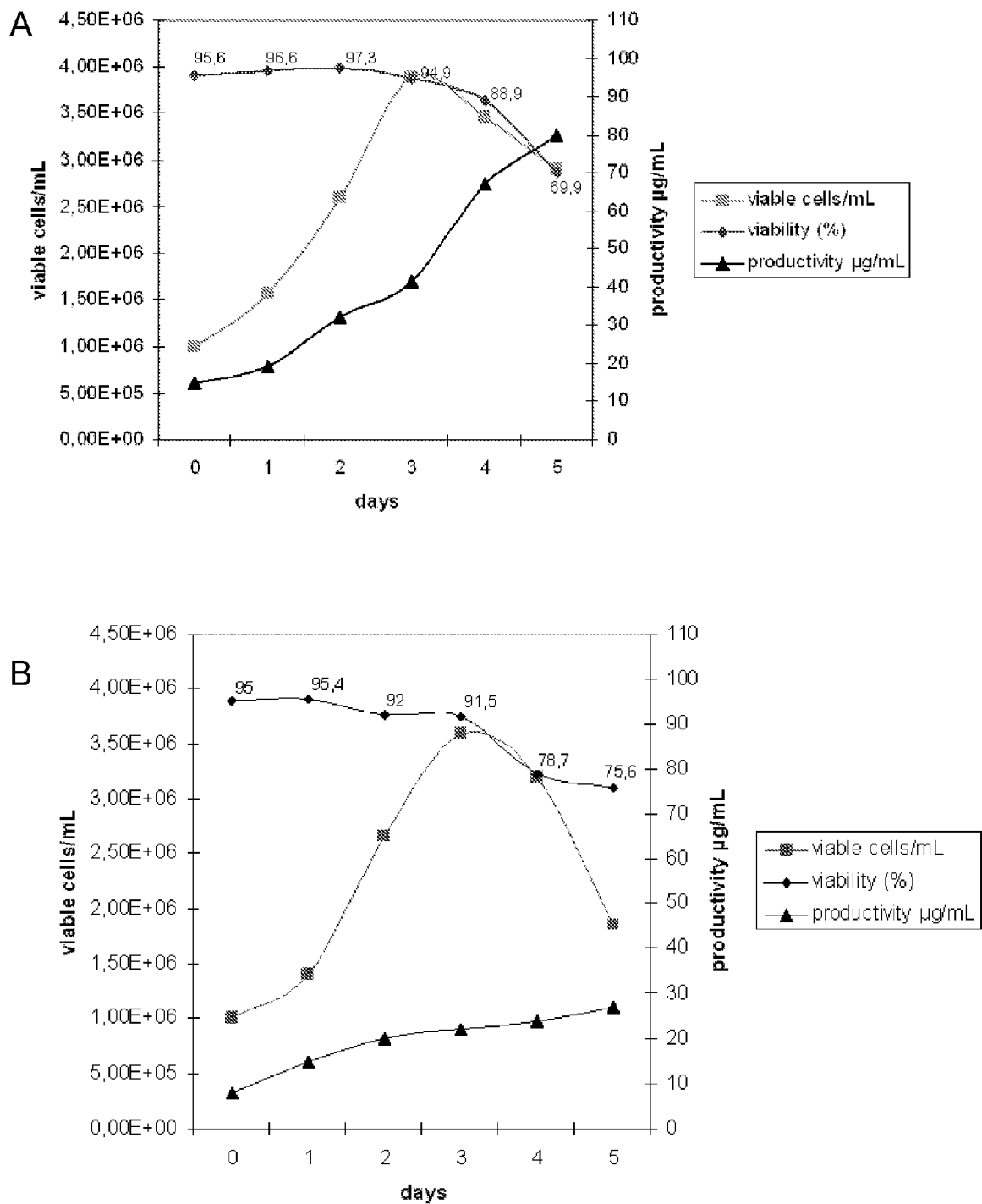

FIG. 2 shows the growth, viability and productivity of the MS24PTX (panel A) and 293F/PTX3/2F12 (panel B) clones in the same seeding and growing conditions. As shown in the figure, with the re-transfection of the PTX3 expressing clone 293F/PTX3/2F12 with a new plasmid in which PTX3 is under the control of CMV promoter (MS24PTX clone) we were able to obtain about 4 fold increase in PTX3 productivity.

Example 5

Purification of Recombinant Human PTX3 from MS24PTX Clone

Culture supernantant from MS24PTX clone, grown in spinner flask, was loaded onto a Q-Sepharose™ Fast Flow (GE Healthcare, UK) packed column. Retained material was eluted using a nonlinear gradient. The PTX3-containing fraction was directly applied to a ceramic Hydroxyapatite (Bio-Rad, Hercules, Calif., USA) packed column. The retained material was eluted by increasing phosphate concentration in a nonlinear fashion. The PTX3-containing fraction was concentrated and buffer changed on a ultrafiltration membrane (Pellicon-Biomax 100, Millipore) than characterized by Size Exclusion Chromatography on Biosep SEC 54000 (Phenomenex) and SDS-PAGE (FIG. 3).

Example 6

Binding of h-PTX3 to FGF2

The binding of purified recombinant hPTX3 to FGF2 was assessed in an ELISA system. A 96-wells plate (Falcon 3912) was coated with 2 µg/ml of FGF2 (Calbiochem) in PBS and incubated overnight at 4° C. Wells were washed with PBS plus 0.1% Triton X-100 (PBS-Tr, washing solution) and blocked with 200 µl of PBS-Tr containing 3% BSA (PBS-B blocking and diluent solution) for 2 hours at room temperature. After washing, binding was performed adding 100 µl of samples, diluted in PBS-B at PTX3 concentrations ranging from 0 to 120 ng/ml, and incubating the plate at 37° C. for 1 hr. After wash, plates were incubated with 100 µl/well of 100 ng/ml rabbit anti-PTX3 polyclonal antibody (1 hr at 37° C.), washed again and incubated with 100 µl of horseradish peroxidase-labeled goat anti-rabbit IgG (1:1000 in PBS-B; 1 hr at 37° C.). After washing, 100 µl of chromogenic substrate 3,3',5,5'-tetramethylbenzidine (TMB) (sigma-Aldrich) were added and after 10-15 min, the reaction was stopped adding 100 µl of HCl 1M and absorbance determined using a Microplate Reader Model 3550 EIA (Bio-Rad, Hercules, Calif., USA). (FIG. 4).

DEPOSIT STATEMENT

Cultures of the following biological material(s) have been deposited with the European Collection of Cell Cultures (ECACC), located at:

Culture Collections

Public Health

England

Porton Down

Salisbury

SP4OJG, UK under conditions that satisfy the requirements of the Budapest Treaty on the International Recognition of the Deposit of Microorganisms for the Purposes of Patent Procedure.

| International Depository Accession Numbers | | |
|---|---|---|
| Deposited Vector | ECACC Accession No. | Date of Deposit Accepted |
| 293F/PTX3/2F12 | 08011001 | 10 Jan. 2008 |
| MS24PTX | 09072902 | 29 Jul. 2009 |

The invention claimed is:

1. An eukaryotic expression vector comprising the sequence of SEQ ID NO: 1.

2. A recombinant cell able to express human long pentraxin PTX3 protein, wherein said recombinant cell comprises the eukaryotic expression vector of claim 1.

3. The recombinant cell of claim 2, wherein the recombinant cell is a recombinant HEK293F cell line.

4. The recombinant cell of claim 3, wherein the recombinant HEK293F cell line is 293F/PTX3/2F12 clone deposited with European Collection of Cell Cultures (ECACC) as Accession No. 08011001.

5. A recombinant cell able to express human long pentraxin PTX3 protein, wherein said recombinant cell is MS24PTX clone deposited with ECACC as Accession Number 09072902.

6. A method of making a recombinant human host cell able to express human long pentraxin PTX3 protein, comprising transfecting a recombinant human host cell already transfected with a vector capable of expressing human long pentraxin PTX3 protein with the eukaryotic expression vector of claim 1 to produce a double-transfected recombinant human host cell.

7. The method of claim 6, wherein the recombinant human host cell already transfected with a vector capable of expressing human long pentraxin PTX3 is 293F/PTX3/2F12 clone deposited with ECACC as Accession No. 08011001.

8. The method according to claim 6 wherein the eukaryotic expression vector comprising the sequence of SEQ ID NO: 1 is linearized.

9. The method of claim 6, further comprising selecting and growing the double-transfected host cell in a culture medium.

10. A process for producing recombinant human long pentraxin PTX3 protein comprising:
   a) co-transfecting contemporarily or sequentially human cells with a first vector having the sequence of SEQ ID NO: 1 and a second vector having the sequence of SEQ ID NO: 2;
   b) selecting and growing the double transfected cells in a culture medium; and
   c) purifying the human long pentraxin PTX3 protein from the culture medium of the double transfected cells.

11. A method of producing human long pentraxin PTX3 protein, comprising
   a) culturing the recombinant host cell of claim 2 in a culture medium; and
   b) purifying human long pentraxin PTX3 protein from the culture medium.

12. A method for producing human long pentraxin PTX3 protein, comprising
   a) transfecting a recombinant human cell already transfected with an expression vector encoding recombinant human long pentraxin PTX3 protein with an eukaryotic expression vector comprising the sequence of SEQ ID NO: 1;
   b) selecting and growing the transfected recombinant human cell comprising the eukaryotic expression vector comprising the sequence of SEQ ID NO: 1 in a culture medium; and
   c) purifying human long pentraxin PTX3 protein from the culture medium of step b).

13. The method of claim 12, wherein the recombinant human cell already transfected with an expression vector encoding recombinant human long pentraxin PTX3 protein is a recombinant HEK293F cell line.

14. The method of claim 13, wherein the recombinant HEK293F cell line is 293F/PTX3/2F12 clone deposited with ECACC as Accession No. 08011001.

15. The method of claim 12, wherein said purifying is by at least one of anionic-exchange chromatography, hydroxyapatite chromatography or size exclusion chromatography.

16. A process for producing recombinant human long pentraxin PTX3 protein comprising the steps of growing a recombinant MS24PTX clone deposited with ECACC as Accession No. 09072902 in a culture medium and purifying the human long pentraxin PTX3 ; protein from the culture medium.

* * * * *

SEQUENCE LISTING

<160> NUMBER OF SEQ ID NOS: 12

<210> SEQ ID NO 1
<211> LENGTH: 7469
<212> TYPE: DNA
<213> ORGANISM: Artificial Sequence
<220> FEATURE:
<223> OTHER INFORMATION: recombinant plasmid pSASSI-HPTX3

<400> SEQUENCE: 1

```
ggatccccg ggctgcagga attccggctc aaactcagct cacttgagag tctcctcccg      60
ccagctgtgg aaagaacttt gcgtctctcc agcaatgcat ctccttgcga ttctgttttg     120
tgctctctgg tctgcagtgt tggccgagaa ctcggatgat tatgatctca tgtatgtgaa     180
tttggacaac gaaatagaca atggactcca tcccactgag gaccccacgc cgtgcgactg     240
cggtcaggag cactcggaat gggacaagct cttcatcatg ctggagaact cgcagatgag     300
agagcgcatg ctgctgcaag ccacggacga cgtcctgcgg ggcgagctgc agaggctgcg     360
ggaggagctg ggccggctcg cggaaagcct ggcgaggccg tgcgcgccgg ggctccccgc     420
agaggccagg ctgaccagtg ctctggacga gctgctgcag gcgacccgcg acgcgggccg     480
caggctggcg cgtatggagg gcgcggaggc gcagcgccca gaggaggcgg ggcgcgccct     540
ggccgcggtg ctagaggagc tgcggcagac gcgagccgac ctgcacgcgg tgcagggctg     600
ggctgcccga agctggctgc cggcaggttg tgaaacagct attttattcc caatgcgttc     660
caagaagatt tttggaagcg tgcatccagt gagaccaatg aggcttgagt cttttagtgc     720
ctgcatttgg gtcaaagcca cagatgtatt aaacaaaacc atcctgtttt cctatgcac      780
aaagaggaat ccatatgaaa tccagctgta tctcagctac caatccatag tgtttgtggt     840
gggtggagag gagaacaaac tggttgctga agccatggtt ccctgggaa ggtgaccca       900
cctgtgcggc acctggaatt cagaggaagg gctcacatcc ttgtgggtaa atggtgaact     960
ggcggctacc actgttgaga tggccacagg tcacattgtt cctgagggag gaatcctgca    1020
gattggccaa gaaaagaatg gctgctgtgt gggtggtggc tttgatgaaa cattagcctt    1080
ctctgggaga ctcacaggct tcaatatctg ggatagtgtt cttagcaatg aagagataag    1140
agagaccgga ggagcagagt cttgtcacat ccgggggaat attgttgggt ggggagtcac    1200
agagatccag ccacatggag gagctcagta tgtttcataa atgttgtgaa actccacttg    1260
aagccaaaga aagaaactca cacttaaaac acatgccagt tgggaaggtc tgaaaactca    1320
gtgcataata ggaacacttg agactaatga agagagagt tgagaccaat ctttatttgt     1380
actggccaaa tactgaataa acagttgaag gaaagacatt ggaaaaagct tagacatgat    1440
aagatacatt gatgagtttg acaaaccac aactagaatg cagtgaaaaa atgctttat      1500
ttgtgaaatt tgtgatgcta ttgctttatt tgtaaccatt ataagctgca ataaacaagt    1560
taacaacaac aattgcattc attttatgtt tcaggttcag ggggaggtgt gggaggtttt    1620
ttaaagcaag taaaacctct acaaatgtgg tatggctgat tatgatccgg ctgcctcgcg    1680
```

```
cgtttcggtg atgacggtga aaacctctga cacatgcagc tcccggagac ggtcacagct    1740
tgtctgtaag cggatgccgg gagcagacaa gcccgtcagg gcgcgtcagc gggtgttggc    1800
gggtgtcggg gcgcagccat gaccggtcga ctctcgaggg ggggcccggg gatccaacgt    1860
tacagttctc cagtgcatgt aatcccttca gttggttggt acaacttgcc aactgggccc    1920
tgttccacat gtgacacggg ggggaccaa acacaaaggg gttctctgac tgtagttgac     1980
atccttataa atggatgtgc acatttgcca acactgagtg gctttcatcc tggagcagac    2040
tttgcagtct gtggactgca acacaacatt gcctttatgt gtaactcttg gctgaagctc    2100
ttacaccaat gctgggggac atgtacctcc caggggccca ggaagactac gggaggctac    2160
accaacgtca atcagagggg cctgtgtagc taccgataag cggaccctca gagggcatt    2220 agcaatagtg tttataaggc ccccttgtta accctaaacg ggtagcatat gcttcccggg    2280
tagtagtata tactatccag actaacccta attcaatagc atatgttacc caacgggaag    2340
catatgctat cgaattaggg ttagtaaaag ggtcctaagg aacagcgatc gatgataagc    2400
tgtcaaacat gagaattctt gaagacgaaa gggcctcgtg atacgcctat ttttataggt    2460
taatgtcatg ataataatgg tttcttagac gtcaggtggc acttttcggg gaaatgtgcg    2520
cggaacccct atttgtttat ttttctaaat acattcaaat atgtatccgc tcatgagaca    2580
ataaccctga taaatgcttc aataatattg aaaaaggaag agtatgagta ttcaacattt    2640
ccgtgtcgcc cttattccct tttttgcggc attttgcctt cctgttttttg ctcacccaga    2700 aacgctggtg aaagtaaaag atgctgaaga tcagttgggt gcacgagtgg gttacatcga    2760
actggatctc aacagcggta agatccttga gagttttcgc cccgaagaac gttttccaat    2820
gatgagcact tttaaagttc tgctatgtgg cgcggtatta tcccgtgttg acgccgggca    2880
agagcaactc ggtcgccgca tacactattc tcagaatgac ttggttgagt actcaccagt    2940
cacagaaaag catcttacgg atggcatgac agtaagagaa ttatgcagtg ctgccataac    3000
catgagtgat aacactgcgg ccaacttact tctgacaacg atcggaggac cgaaggagct    3060
aaccgctttt ttgcacaaca tgggggatca tgtaactcgc cttgatcgtt gggaaccgga    3120
gctgaatgaa gccataccaa acgacgagcg tgacaccacg atgcctgcag caatggcaac    3180
aacgttgcgc aaactattaa ctggcgaact acttactcta gcttcccggc aacaattaat    3240
agactggatg gaggcggata aagttgcagg accacttctg cgctcggccc ttccggctgg    3300
ctggtttatt gctgataaat ctggagccgg tgagcgtggg tctcgcggta tcattgcagc    3360
actggggcca gatggtaagc cctcccgtat cgtagttatc tacacgacgg ggagtcaggc    3420
aactatggat gaacgaaata gacagatcgc tgagataggt gcctcactga ttaagcattg    3480
gtaactgtca gaccaagttt actcatatat actttagatt gatttaaaac ttcattttta    3540
atttaaaagg atctaggtga agatcctttt tgataatctc atgaccaaaa tcccttaacg    3600
tgagttttcg ttccactgag cgtcagaccc cgtagaaaag atcaaggat cttcttgaga    3660 tcctttttttt ctgcgcgtaa tctgctgctt gcaaacaaaa aaaccaccgc taccagcggt    3720
ggtttgtttg ccggatcaag agctaccaac tctttttccg aaggtaactg gcttcagcag    3780
agcgcagata ccaaatactg tccttctagt gtagccgtag ttaggccacc acttcaagaa    3840
ctctgtagca ccgcctacat acctcgctct gctaatcctg ttaccagtgg ctgctgccag    3900
tggcgataag tcgtgtctta ccgggttgga ctcaagacga tagttaccgg ataaggcgca    3960
gcggtcgggc tgaacggggg gttcgtgcac acagcccagc ttggagcgaa cgacctacac    4020
```

```
cgaactgaga tacctacagc gtgagctatg agaaagcgcc acgcttcccg aagggagaaa    4080
ggcggacagg tatccggtaa gcggcagggt cggaacagga gagcgcacga gggagcttcc    4140
aggggggaaac gcctggtatc tttatagtcc tgtcgggttt cgccacctct gacttgagcg    4200
tcgattttg tgatgctcgt caggggggcg gagcctatgg aaaaacgcca gcaacgcggc    4260
cttttacgg ttcctggcct tttgctgcgc cgcgtgcggc tgctggagat ggcggacgcg    4320
atggatatgt tctgccaagg gttggttttgc gcattcacag ttctccgcaa gaattgattg    4380
gctccaattc ttggagtggt gaatccgtta gcgaggtgcc gccggcttcc attcaggtcg    4440
aggtggcccg gctccatgca ccgcgacgca acgcggggag gcagacaagg tatagggcgg    4500
cgcctacaat ccatgccaac ccgttccatg tgctcgccga ggcggcataa atcgccgtga    4560
cgatcagcgg tccagtgatc gaagttaggc tggtaagagc cgcgagcgat ccttgaagct    4620
gtccctgatg gtcgtcatct acctgcctgg acagcatggc ctgcaacgcg ggcatcccga    4680
tgccgccgga agcgagaaga atcataatgg ggaaggccat ccagcctcgc gtcgcgaacg    4740
gcgaacgcca gcaagacgta gcccagcgcg tcggccgcca tgccctgctt catccccgtg    4800
gcccgttgct cgcgtttgct ggcggtgtcc ccggaagaaa tatatttgca tgtctttagt    4860
tctatgatga cacaaacccc gcccagcgtc ttgtcattgg cgaattcgaa cacgcagatg    4920
cagtcggggc ggcgcggtcc caggtccact tcgcatatta aggtgacgcg tgtggcctcg    4980
aacaccgagc gaccctgcag cgacccgctt aacagcgtca acagcgtgcc gcagatcccg    5040
ggcaatgaga tatgaaaaag cctgaactca ccgcgacgtc tgtcgagaag tttctgatcg    5100
aaaagttcga cagcgtctcc gacctgatgc agctctcgga gggcgaagaa tctcgtgctt    5160
tcagcttcga tgtaggaggg cgtggatatg tcctgcgggt aaatagctgc gccgatggtt    5220
tctacaaaga tcgttatgtt tatcggcact ttgcatcggc cgcgctcccg attccggaag    5280
tgcttgacat tggggaattc agcgagagcc tgacctattg catctcccgc cgtgcacagg    5340
gtgtcacgtt gcaagacctg cctgaaaccg aactgcccgc tgttctgcag ccggtcgcgg    5400
aggccatgga tgcgatcgct gcggccgatc ttagccagac gagcgggttc ggcccattcg    5460
gaccgcaagg aatcggtcaa tacactacat ggcgtgattt catatgcgcg attgctgatc    5520
cccatgtgta tcactggcaa actgtgatgg acgacaccgt cagtgcgtcc gtcgcgcagg    5580
ctctcgatga gctgatgctt tgggccgagg actgccccga agtccggcac ctcgtgcacg    5640
cggatttcgg ctccaacaat gtcctgacgg acaatggccg cataacagcg gtcattgact    5700
ggagcgaggc gatgttcggg gattcccaat acgaggtcgc caacatcttc ttctggaggc    5760
cgtggttggc ttgtatggag cagcagacgc gctacttcga gcggaggcat ccggagcttg    5820
caggatcgcc gcggctccgg gcgtatatgc tccgcattgg tcttgaccaa ctctatcaga    5880
gcttggttga cggcaatttc gatgatgcag cttgggcgca gggtcgatgc gacgcaatcg    5940
tccgatccgg agccgggact gtcgggcgta cacaaatcgc ccgcagaagc gcggccgtct    6000
ggaccgatgg ctgtgtagaa gtactcgccg atagtggaaa ccgacgcccc agcactcgtc    6060
cgagggcaaa ggaataggg agatggggga ggctaactga acacggaag gagacaatac    6120
cggaaggaac ccgcgctatg acggcaataa aagacagaa taaaacgcac gggtgttggg    6180
tcgtttgttc ataaacgcgg ggttcggtcc cagggctggc actctgtcga taccccaccg    6240
agaccccatt ggggccaata cgcccgcgtt tcttccttttt ccccaccccca cccccaagt    6300
tcgggtgaag gcccagggct cgcagccaac gtcgggcgg caggccctgc catagccact    6360
ggccccgtgg gttagggacg gggtccccca tggggaatgg tttatggttc gtgggggtta    6420
```

```
ttattttggg cgttgcgtgg ggtctggtcc acgactggac tgagcagaca gacccatggt   6480
ttttggatgg cctgggcatg gaccgcatgt actggcgcga cacgaacacc gggcgtctgt   6540
ggctgccaaa cacccccgac ccccaaaaac caccgcgcgg atttctggcg tgccaagcta   6600
gtcgaccaat tctcatgttt gacagcttat catcgcagat ccgggcaacg ttgttgccat   6660
tgctgcaggc gcagaactgg taggtatgga agatctatac attgaatcaa tattggcaat   6720
tagccatatt agtcattggt tatatagcat aaatcaatat tggctattgg ccattgcata   6780
cgttgtatct atatcataat atgtacattt atattggctc atgtccaata tgaccgccat   6840
gttgacattg attattgact agttattaat agtaatcaat tacggggtca ttagttcata   6900
gcccatatat ggagttccgc gttacataac ttacggtaaa tggcccgcct ggctgaccgc   6960
ccaacgaccc ccgcccattg acgtcaataa tgacgtatgt tcccatagta acgccaatag   7020
ggactttcca ttgacgtcaa tgggtggagt atttacggta aactgcccac ttggcagtac   7080
atcaagtgta tcatatgcca agtccgcccc ctattgacgt caatgacggt aaatggcccg   7140
cctggcatta tgcccagtac atgaccttac gggactttcc tacttggcag tacatctacg   7200
tattagtcat cgctattacc atggtgatgc ggttttggca gtacaccaat gggcgtggat   7260
agcggtttga ctcacgggga tttccaagtc tccaccccat tgacgtcaat gggagtttgt   7320
tttggcacca aaatcaacgg gactttccaa aatgtcgtaa taaccccgcc ccgttgacgc   7380
aaatgggcgg taggcgtgta cggtgggagg tctatataag cagagctcgt ttagtgaacc   7440
gtcagatctc tagaagctgg gtaccagct                                     7469
```

<210> SEQ ID NO 2
<211> LENGTH: 6796
<212> TYPE: DNA
<213> ORGANISM: Artificial Sequence
<220> FEATURE:
<223> OTHER INFORMATION: recombinant plasmid pSC1-PTX3

<400> SEQUENCE: 2

```
aattcggatc cccgggctg caggaattcc ggctcaaact cagctcactt gagagtctcc     60
tcccgccagc tgtggaaaga actttgcgtc tctccagcaa tgcatctcct tgcgattctg    120
ttttgtgctc tctggtctgc agtgttggcc gagaactcgg atgattatga tctcatgtat    180
gtgaatttgg acaacgaaat agacaatgga ctccatccca ctgaggaccc cacgccgtgc    240
gactgcggtc aggagcactc ggaatgggac aagctcttca tcatgctgga gaactcgcag    300
atgagagagc gcatgctgct gcaagccacg gacgacgtcc tgcggggcga gctgcagagg    360
ctgcgggagg agctgggccg gctcgcggaa agcctggcga ggccgtgcgc gccgggggct    420
cccgcagagg ccaggctgac cagtgctctg gacgagctgc tgcaggcgac ccgcgacgcg    480
ggccgcaggc tggcgcgtat ggagggcgcg gaggcgcagc gcccagagga ggcggggcgc    540
gccctggccg cggtgctaga ggagctgcgg cagacgcgag ccgacctgca cgcggtgcag    600
ggctgggctg cccggagctg gctgccggca ggttgtgaaa cagctatttt attcccaatg    660
cgttccaaga agatttttgg aagcgtgcat ccagtgagac caatgaggct tgagtctttt    720
agtgcctgca tttgggtcaa agccacagat gtattaaaca aaaccatcct gttttcctat    780
ggcacaaaga ggaatccata tgaaatccag ctgtatctca gctaccaatc catagtgttt    840
gtggtgggtg gagaggagaa caaactggtt gctgaagcca tggtttccct gggaaggtgg    900
acccacctgt gcggcacctg gaattcagag gaagggctca catccttgtg ggtaaatggt    960
```

```
gaactggcgg ctaccactgt tgagatggcc acaggtcaca ttgttcctga gggaggaatc    1020
ctgcagattg gccaagaaaa gaatggctgc tgtgtgggtg gtggctttga tgaaacatta    1080
gccttctctg ggagactcac aggcttcaat atctgggata gtgttcttag caatgaagag    1140
ataagagaga ccgaggagc agagtcttgt cacatccggg ggaatattgt tgggtgggga    1200
gtcacagaga tccagccaca tggaggagct cagtatgttt cataaatgtt gtgaaactcc    1260
acttgaagcc aaagaaagaa actcacactt aaaacacatg ccagttggga aggtctgaaa    1320
actcagtgca taataggaac acttgagact aatgaaagag agagttgaga ccaatcttta    1380
tttgtactgg ccaaatactg aataaacagt tgaaggaaag acattggaaa agcttatcg    1440 ataccgtcga cctcgagggg gggcccgggg atccagatct tattaaagca gaacttgttt    1500
attgcagctt ataatggtta caaataaagc aatagcatca caaatttcac aaataaagca    1560 ttttttttcac tgcattctag ttgtggtttg tccaaactca tcaatgtatc ttatcatgtc    1620
tggtcgactc tagactcttc cgcttcctcg ctcactgact cgctgcgctc ggtcgttcgg    1680
ctgcggcgag cggtatcagc tcactcaaag gcggtaatac ggttatccac agaatcaggg    1740
gataacgcag gaaagaacat gtgccccagg aggcagaagt atgcaaagca tgcatctcaa    1800
ttagtcagca accaggtgtg gaaagtcccc aggctcccca gcaggcagaa gtatgcaaag    1860
catgcatctc aattagtcag caaccatagt cccgccccta actccgccca tcccgcccct    1920
aactccgccc agttccgccc attctccgcc ccatggctga ctaatttttt ttatttatgc    1980
agaggccgag gccgcctctg cctctgagct attccagaag tagtgaggag ctttttttgg    2040
aggcctaggc ttttgcaaaa agctcccggg agcttgtata tccattttcg gatctgatca    2100
agagacagga tgaggatcgt ttcgcatgat tgaacaagat ggattgcacg caggttctcc    2160
ggccgcttgg gtgagaggc tattcggcta tgactgggca caacagacaa tcggctgctc    2220
tgatgccgcc gtgttccggc tgtcagcgca ggggcgcccg gttcttttg tcaagaccga    2280 cctgtccggt gccctgaatg aactgcagga cgaggcagcg cggctatcgt ggctggccac    2340
gacgggcgtt ccttgcgcag ctgtgctcga cgttgtcact gaagcgggaa gggactggct    2400
gctattgggc gaagtgccgg ggcaggatct cctgtcatct caccttgctc ctgccgagaa    2460
agtatccatc atggctgatg caatgcggcg gctgcatacg cttgatccgg ctacctgccc    2520
attcgaccac caagcgaaac atcgcatcga gcgagcacgt actcggatgg aagccggtct    2580
tgtcgatcag gatgatctgg acgaagagca tcaggggctc gcgccagccg aactgttcgc    2640
caggctcaag gcgcgcatgc ccgacggcga ggatctcgtc gtgacccatg gcgatgcctg    2700
cttgccgaat atcatggtgg aaaatggccg cttttctgga ttcatcgact gtggccggct    2760
gggtgtggcg gaccgctatc aggacatagc gttggctacc cgtgatattg ctgaagagct    2820
tggcggcgaa tgggctgacc gcttcctcgt gctttacggt atcgccgctc ccgattcgca    2880
gcgcatcgcc ttctatcgcc ttcttgacga gttcttctga gcgggactct ggggttcgaa    2940
atgaccgacc aagcgacgcc caacctgcca tcacagagatt cgattccac cgccgccttc    3000 tatgaaaggt tgggcttcgg aatcgttttc cgggacgccg gctggatgat cctccagcgc    3060
ggggatctca tgctggagtt cttcgcccac cccaacttgt ttattgcagc ttataatggt    3120
tacaaataaa gcaatagcat cacaaatttc acaaataaag catttttttc actgcattct    3180
agttgtggtt tgtccaaact catcaatgta tcttatcatg tctgtataca tgtgagcaaa    3240
aggccagcaa aaggccagga accgtaaaaa ggccgcgttg ctggcgtttt tccataggct    3300
ccgcccccct gacgagcatc acaaaaatcg acgctcaagt cagaggtggc gaaacccgac    3360
```

```
aggactataa agataccagg cgtttccccc tggaagctcc ctcgtgcgct ctcctgttcc    3420
gaccctgccg cttaccggat acctgtccgc ctttctccct tcgggaagcg tggcgctttc    3480
tcaatgctca cgctgtaggt atctcagttc ggtgtaggtc gttcgctcca agctgggctg    3540
tgtgcacgaa ccccccgttc agcccgaccg ctgcgcctta ccggtaact atcgtcttga     3600 gtccaacccg gtaagacacg acttatcgcc actggcagca gccactggta acaggattag    3660
cagagcgagg tatgtaggcg gtgctacaga gttcttgaag tggtggccta actacggcta    3720
cactagaagg acagtatttg gtatctgcgc tctgctgaag ccagttacct tcggaaaaag    3780
agttggtagc tcttgatccg gcaaacaaac caccgctggt agcggtggtt tttttgtttg    3840
caagcagcag attacgcgca gaaaaaaagg atctcaagaa gatcctttga tcttttctac    3900
ggggtctgac gctcagtgga acgaaaactc acgttaaggg attttggtca tgagattatc    3960
aaaaaggatc ttcacctaga tccttttaaa ttaaaaatga agttttaaat caatctaaag    4020
tatatatgag taaacttggt ctgacagtta ccaatgctta atcagtgagg cacctatctc    4080
agcgatctgt ctatttcgtt catccatagt tgcctgactc cccgtcgtgt agataactac    4140
gatacgggag ggcttaccat ctggccccag tgctgcaatg ataccgcgag acccacgctc    4200
accggctcca gatttatcag caataaacca gccagccgga agggccgagc gcagaagtgg    4260
tcctgcaact ttatccgcct ccatccagtc tattaattgt tgccgggaag ctagagtaag    4320
tagttcgcca gttaatagtt tgcgcaacgt tgttgccatt gctacaggca tcgtggtgtc    4380
acgctcgtcg tttggtatgg cttcattcag ctccggttcc caacgatcaa ggcgagttac    4440
atgatccccc atgttgtgca aaaaagcggt tagctccttc ggtcctccga tcgttgtcag    4500
aagtaagttg gccgcagtgt tatcactcat ggttatggca gcactgcata attctcttac    4560
tgtcatgcca tccgtaagat gcttttctgt gactggtgag tactcaacca agtcattctg    4620
agaatagtgt atgcggcgac cgagttgctc ttgcccggcg tcaatacggg ataataccgc    4680
gccacatagc agaactttaa aagtgctcat cattggaaaa cgttcttcgg ggcgaaaact    4740
ctcaaggatc ttaccgctgt tgagatccag ttcgatgtaa cccactcgtg cacccaactg    4800
atcttcagca tcttttactt tcaccagcgt ttctgggtga gcaaaaacag gaaggcaaaa    4860
tgccgcaaaa aagggaataa gggcgacacg gaaatgttga atactcatac tcttcttttt    4920
tcaatattat tgaagcattt atcagggtta ttgtctcatg agcggataca tatttgaatg    4980
tatttagaaa aataaacaaa tagggggttcc gcgcacattt ccccgaaaag tgccacctga   5040
cgtctaagaa accattatta tcatgacatt aacctataaa aataggcgta tcacgaggcc    5100 ctttcgtct cgcgcgtttc ggtgatgacg gtgaaaacct ctgacacatg cagctcccgg     5160
agacggtcac agcttgtctg taagcggatg ccgggagcag acaagcccgt cagggcgcgt    5220
cagcgggtgt tggcgggtgt cggggctggc ttaactatgc ggcatcagag cagattgtac    5280
tgagagtgca ccatatgcgg tgtgaaatac cgcacagatg cgtaaggaga aaataccgca    5340
tcaggaaatt gtaaacgtta atattttgtt aaaattcgcg ttaaattttt gttaaatcag    5400 ctcattttt aaccaatagg ccgaaatcgg caaaatccct tataaatcaa agaatagac      5460 cgagataggg ttgagtgttg ttccagtttg gaacaagagt ccactattaa agaacgtgga    5520
ctccaacgtc aaagggcgaa aaaccgtcta tcagggcgat ggcccactac gtgatctggc    5580
ctccgcgccg ggtttggcg ccccccgcgg gcgcccccct cctcacgcg agcgctgcca      5640 cgtcagacga agggcgcagc gagcgtcctg atccttccgc ccggacgctc aggacagcgg    5700
```

```
cccgctgctc ataagactcg gccttagaac cccagtatca gcagaaggac attttaggac    5760
gggacttggg tgactctagg gcactggttt tctttccaga gagcggaaca ggcgaggaaa    5820
agtagtccct tctcggcgat tctgcggagg gatctccgtg gggcggtgaa cgccgatgat    5880
tatataagga gcgccgggt gtggcacagc tagttccgtc gcagccggga tttgggtcgc     5940
ggttcttgtt tgtggatcgc tgtgatcgtc acttggtgag tagcgggctg ctgggctggc    6000
cggggctttc gtggccgccg ggccgctcgg tgggacggaa gcgtgtggag agaccgccaa    6060
gggctgtagt ctgggtccgc gagcaaggtt gccctgaact gggggttggg gggagcgcag    6120
caaaatggcg gctgttcccg agtcttgaat ggaagacgct tgtgaggcgg gctgtgaggt    6180
cgttgaaaca aggtgggggg catggtgggc ggcaagaacc caaggtcttg aggccttcgc    6240
taatgcggga aagctcttat tcgggtgaga tgggctgggg caccatctgg ggaccctgac    6300
gtgaagtttg tcactgactg gagaactcgg tttgtcgtct gttgcggggg cggcagttat    6360
ggcggtgccg ttgggcagtg caccgtacc tttgggagcg cgcgccctcg tcgtgtcgtg      6420
acgtcacccg ttctgttggc ttataatgca gggtgggcc acctgccggt aggtgtgcgg     6480
taggcttttc tccgtcgcag gacgcagggt tcgggcctag ggtaggctct cctgaatcga    6540
caggcgccgg acctctggtg aggggaggga taagtgaggc gtcagtttct ttggtcggtt    6600
ttatgtacct atcttcttaa gtagctgaag ctccggtttt gaactatgcg ctcggggttg    6660
gcgagtgtgt tttgtgaagt tttttaggca ccttttgaaa tgtaatcatt tgggtcaata    6720
tgtaattttc agtgttagac tagtaaattg tccgctaaat tctggccgtt tttggctttt    6780
ttgttagacc ggaccg                                                    6796

<210> SEQ ID NO 3
<211> LENGTH: 26
<212> TYPE: DNA
<213> ORGANISM: Artificial Sequence
<220> FEATURE:
<223> OTHER INFORMATION: synthetic primer

<400> SEQUENCE: 3
atatcacgtg atctggcctc cgcgcc                                         26

<210> SEQ ID NO 4
<211> LENGTH: 23
<212> TYPE: DNA
<213> ORGANISM: Artificial Sequence
<220> FEATURE:
<223> OTHER INFORMATION: synthetic primer

<400> SEQUENCE: 4
ggaattcggt ccggtctaac aaa                                            23

<210> SEQ ID NO 5
<211> LENGTH: 26
<212> TYPE: DNA
<213> ORGANISM: Artificial Sequence
<220> FEATURE:
<223> OTHER INFORMATION: synthetic primer

<400> SEQUENCE: 5
atatacatgt ccccaggcag gcagaa                                         26

<210> SEQ ID NO 6
<211> LENGTH: 26
<212> TYPE: DNA
<213> ORGANISM: Artificial Sequence
```

```
<220> FEATURE:
<223> OTHER INFORMATION: synthetic primer

<400> SEQUENCE: 6
atatacatgt atacagacat gataag                                          26

<210> SEQ ID NO 7
<211> LENGTH: 23
<212> TYPE: DNA
<213> ORGANISM: Artificial Sequence
<220> FEATURE:
<223> OTHER INFORMATION: synthetic primer

<400> SEQUENCE: 7
gtgagaactc ggatgattat gat                                             23

<210> SEQ ID NO 8
<211> LENGTH: 23
<212> TYPE: DNA
<213> ORGANISM: Artificial Sequence
<220> FEATURE:
<223> OTHER INFORMATION: synthetic primer

<400> SEQUENCE: 8
tgaaacatac tgagctcctc cat                                             23

<210> SEQ ID NO 9
<211> LENGTH: 27
<212> TYPE: DNA
<213> ORGANISM: Artificial Sequence
<220> FEATURE:
<223> OTHER INFORMATION: synthetic primer

<400> SEQUENCE: 9
gagaactgta acgttggatc cagctgg                                         27

<210> SEQ ID NO 10
<211> LENGTH: 27
<212> TYPE: DNA
<213> ORGANISM: Artificial Sequence
<220> FEATURE:
<223> OTHER INFORMATION: synthetic primer

<400> SEQUENCE: 10
gtgtacaaag gatccagaca tgataag                                         27

<210> SEQ ID NO 11
<211> LENGTH: 26
<212> TYPE: DNA
<213> ORGANISM: Artificial Sequence
<220> FEATURE:
<223> OTHER INFORMATION: synthetic primer

<400> SEQUENCE: 11
aagcttagac atgataagat acattg                                          26

<210> SEQ ID NO 12
<211> LENGTH: 26
<212> TYPE: DNA
<213> ORGANISM: Artificial Sequence
<220> FEATURE:
<223> OTHER INFORMATION: synthetic primer

<400> SEQUENCE: 12
ctcgagagtc gaccggtcat ggctgc                                          26
```